US011633159B2

(12) United States Patent
Chakravarthy et al.

(10) Patent No.: US 11,633,159 B2
(45) Date of Patent: Apr. 25, 2023

(54) PERSONALIZATION OF ARTIFICIAL INTELLIGENCE MODELS FOR ANALYSIS OF CARDIAC RHYTHMS

(71) Applicant: Medtronic, Inc., Minneapolis, MN (US)

(72) Inventors: Niranjan Chakravarthy, Singapore (SG); Siddharth Dani, Minneapolis, MN (US); Tarek D. Haddad, Minneapolis, MN (US); Rodolphe Katra, Blaine, MN (US); Donald R. Musgrove, Minneapolis, MN (US); Lindsay A. Pedalty, Minneapolis, MN (US); Andrew Radtke, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 363 days.

(21) Appl. No.: 16/850,618

(22) Filed: Apr. 16, 2020

(65) Prior Publication Data
US 2020/0352522 A1 Nov. 12, 2020

Related U.S. Application Data

(60) Provisional application No. 62/843,693, filed on May 6, 2019.

(51) Int. Cl.
*A61B 5/00* (2006.01)
*A61B 5/35* (2021.01)
*A61B 5/341* (2021.01)

(52) U.S. Cl.
CPC ............ *A61B 5/7267* (2013.01); *A61B 5/341* (2021.01); *A61B 5/35* (2021.01); *A61B 5/0006* (2013.01); *A61B 5/686* (2013.01)

(58) Field of Classification Search
CPC ........ G16H 50/20; G16H 50/30; G16H 50/70; G16H 50/50; A61B 5/7267; A61B 5/7264;
(Continued)

(56) References Cited

U.S. PATENT DOCUMENTS 7,490,085 B2 * 2/2009 Walker ................... G16H 30/40
600/125
2018/0374105 A1 12/2018 Azout et al.

OTHER PUBLICATIONS

International Search Report and Written Opinion of International Application No. PCT/US2020/029431, dated Jul. 15, 2020, 13 pp.
(Continued)

*Primary Examiner* — Deborah L Malamud
(74) *Attorney, Agent, or Firm* — Shumaker & Sieffert, P.A.

(57) ABSTRACT

Techniques are disclosed for monitoring a patient for the occurrence of cardiac arrhythmias. A computing system obtains a cardiac electrogram (EGM) strip for a current patient. Additionally, the computing system may apply a first cardiac rhythm classifier (CRC) with a segment of the cardiac EGM strip as input. The first CRC is trained on training cardiac EGM strips from a first population. The first CRC generates first data regarding an aspect of a cardiac rhythm of the current patient. The computing system may also apply a second CRC with the segment of the cardiac EGM strip as input. The second CRC is trained on training cardiac EGM strips from a smaller, second population. The second CRC generates second data regarding the aspect of the cardiac rhythm of the current patient. The computing system may generate output data based on the first and/or second data.

17 Claims, 11 Drawing Sheets

(58) Field of Classification Search
CPC ... A61B 5/0006; A61B 5/7275; A61B 5/0022; A61B 5/318; A61B 5/0245; A61B 5/28; A61B 5/346; A61B 5/35; A61B 5/486; A61B 5/00; A61B 5/0004; A61B 5/02; A61B 5/7228; G06N 20/00; A61N 1/37; A61N 1/3702; A61N 1/365
See application file for complete search history.

(56) References Cited

OTHER PUBLICATIONS

Andersen et al., "A Deep Learning Approach for Real-Time Detection of Atrial Fibrillation," Expert Systems With Applications, vol. 115, Aug. 14, 2018, pp. 465-473.

* cited by examiner

PERSONALIZATION OF ARTIFICIAL INTELLIGENCE MODELS FOR ANALYSIS OF CARDIAC RHYTHMS

This application claims the benefit of U.S. Provisional Patent Application 62/843,693, filed May 6, 2019, the entire content of which is incorporated herein by reference.

FIELD

This disclosure generally relates to health monitoring and, more particularly, to monitoring cardiac health.

BACKGROUND

Malignant tachyarrhythmia, for example, ventricular fibrillation, is an uncoordinated contraction of the cardiac muscle of the ventricles in the heart and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes.

An implanted or non-implanted medical device may monitor a patient's heart for cardiac arrhythmias. A user, such as a physician, may review data generated by the medical device for occurrences of cardiac arrhythmias, e.g., atrial or ventricular tachyarrhythmia, or asystole. The user may diagnose a medical condition of the patient based on the occurrences of the cardiac arrhythmias.

SUMMARY

In general, the disclosure describes techniques for personalizing artificial intelligence (AI) models that analyze cardiac rhythms of a patient or specializing AI models for a patient cohort. As discussed in this disclosure, a computing system may obtain a cardiac electrogram (EGM) strip, e.g., data representing a sequence of values of the cardiac EGM waveform over a period of time, for a current patient. Additionally, the computing system may apply a first cardiac rhythm classifier (CRC) with a segment of the cardiac EGM strip as input. The first CRC is trained on training cardiac EGM strips from a first population. The first CRC generates first data regarding an aspect of a cardiac rhythm of the current patient. The computing system may also apply a second CRC with the segment of the cardiac EGM strip as input. The second CRC is trained on training cardiac EGM strips from a smaller, second population. The second CRC generates second data regarding the aspect of the cardiac rhythm of the current patient. The computing system may generate output data based on the first and/or second data.

In one aspect, this disclosure describes a method comprising: obtaining, by a computing system, a cardiac electrogram (EGM) strip for a current patient; applying, by the computing system, a first cardiac rhythm classifier neural network (CRC) with a segment of the cardiac EGM strip as input, wherein: the first CRC is trained on training cardiac EGM strips from a first population that includes a plurality of patients, the first CRC generates, based on the segment of the cardiac EGM strip, first data regarding an aspect of a cardiac rhythm of the current patient; applying, by the computing system, a second CRC with the segment of the cardiac EGM strip as input, wherein: the second CRC is a version of the first CRC that is trained on training cardiac EGM strips from a second population that is smaller than the first population, the second CRC generates, based on the segment of the cardiac EGM strip, second data regarding the aspect of the cardiac rhythm of the current patient; and generating, by the computing system, output data based on the first data and the second data.

In another aspect, this disclosure describes a method comprising: obtaining, by a computing system, a cardiac EGM strip for a current patient; applying, by the computing system, a specialized cardiac rhythm classifier (CRC) with a segment of the cardiac EGM strip as input, wherein: the specialized CRC is trained on training cardiac EGM strips from the current patient, and the specialized CRC generates, based on the segment of the cardiac EGM strip, first data regarding an aspect of a cardiac rhythm of the current patient; generating, by the computing system, output data based on the first data and historical data generated by the specialized CRC based on earlier cardiac EGM strips from the current patient.

In another aspect, this disclosure describes a computing system comprising processing circuitry and a storage medium, the computing device configured to perform these methods. In another aspect, this disclosure describes a computer-readable data storage medium having instructions stored thereon that, when executed, cause a computing system to perform these methods.

In another aspect, this disclosure describes a computing system comprising: a storage medium configured to store a cardiac electrogram (EGM) strip for a current patient; and processing circuitry configured to: apply a first cardiac rhythm classifier neural network (CRC) with a segment of the cardiac EGM strip as input, wherein: the first CRC is trained on training cardiac EGM strips from a first population that includes a plurality of patients, the first CRC generates, based on the segment of the cardiac EGM strip, first data regarding an aspect of a cardiac rhythm of the current patient; apply a second CRC with the segment of the cardiac EGM strip as input, wherein: the second CRC is a version of the first CRC that is trained on training cardiac EGM strips from a second population that is smaller than the first population, the second CRC generates, based on the segment of the cardiac EGM strip, second data regarding the aspect of the cardiac rhythm of the current patient; and generate output data based on the first data and the second data.

In another aspect, this disclosure describes a computer-readable data storage medium having instructions stored thereon that, when executed, cause a computing system to: obtain a cardiac electrogram (EGM) strip for a current patient; apply a first cardiac rhythm classifier neural network (CRC) with a segment of the cardiac EGM strip as input, wherein: the first CRC is trained on training cardiac EGM strips from a first population that includes a plurality of patients, the first CRC generates, based on the segment of the cardiac EGM strip, first data regarding an aspect of a cardiac rhythm of the current patient; apply a second CRC with the segment of the cardiac EGM strip as input, wherein: the second CRC is a version of the first CRC that is trained on training cardiac EGM strips from a second population that is smaller than the first population, the second CRC generates, based on the segment of the cardiac EGM strip, second data regarding the aspect of the cardiac rhythm of the current patient; and generate output data based on the first data and the second data.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
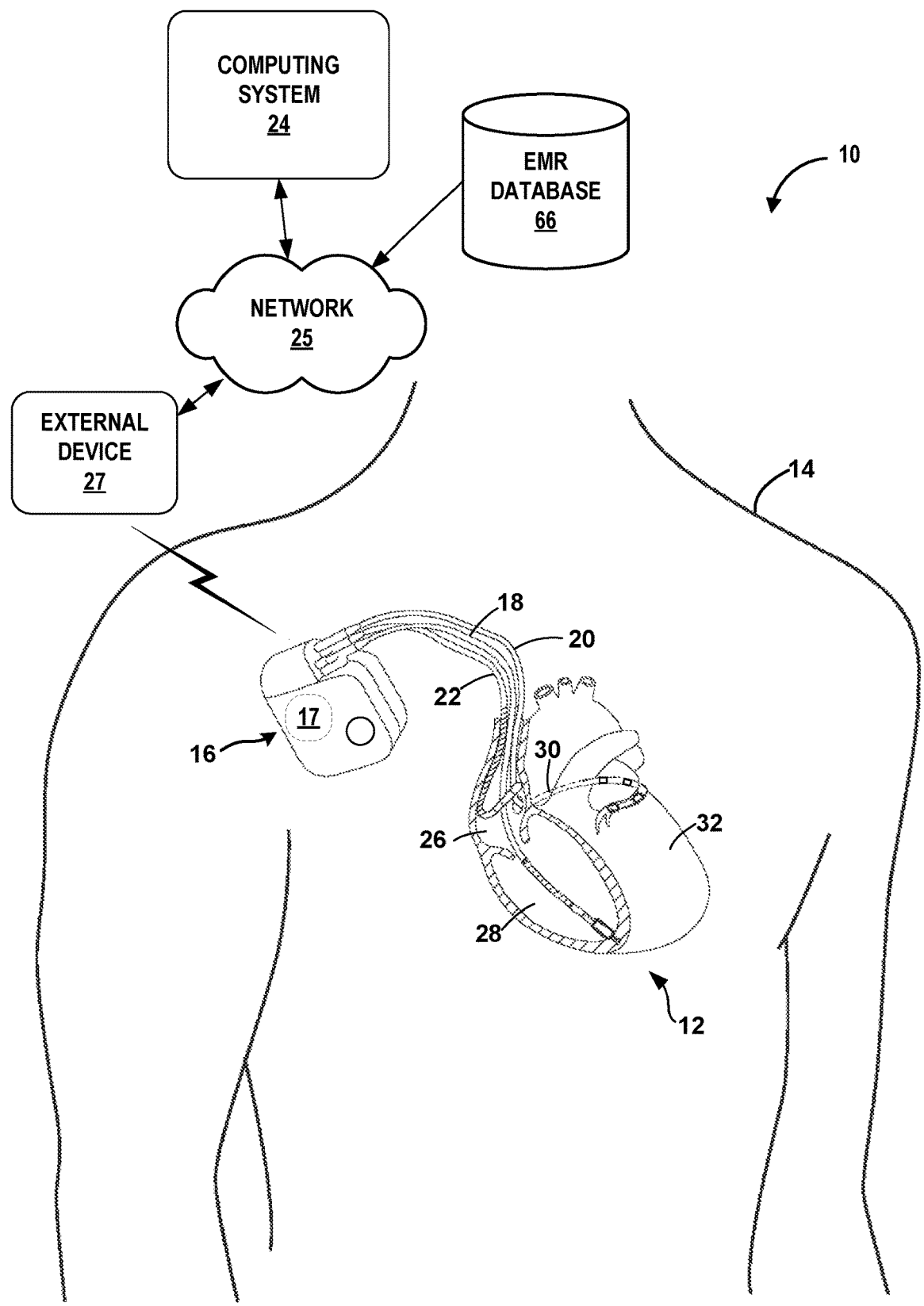
FIG. 1 is a block diagram illustrating a system for analyzing one or more aspects of a cardiac rhythm of a patient in accordance with the techniques of the disclosure.

FIG. 1 is a block diagram illustrating a system 10 for analyzing one or more aspects of a cardiac rhythm of a patient 14 in accordance with the techniques of the disclosure. System 10 includes a medical device 16. One example of such a medical device is an implantable medical device (IMD), as shown in FIG. 1. As illustrated by example system 10 in FIG. 1, medical device 16 may, in some examples, be an implantable cardiac monitor, an implantable cardiac pacemaker, implantable cardioverter/defibrillator (ICD), or pacemaker/cardioverter/defibrillator, for example. In some examples, medical device 16 is a non-implantable medical device, such as a non-implantable cardiac monitor (e.g., a Holter monitor).

In the example of FIG. 1, medical device 16 is connected to leads 18, 20 and 22 and is communicatively coupled to external device 27, which in turn is communicatively coupled to computing system 24 over communication network 25. Medical device 16 senses electrical signals attendant to the depolarization and repolarization of heart 12, e.g., a cardiac electrogram (EGM), via electrodes on one or more leads 18, 20 and 22 or the housing of medical device 16. Medical device 16 may also deliver therapy in the form of electrical signals to heart 12 via electrodes located on one or more leads 18, 20 and 22 or a housing of medical device 16. The therapy may be pacing, cardioversion and/or defibrillation pulses. Medical device 16 may monitor cardiac EGM signals collected by electrodes on leads 18, 20 or 22, and based on the cardiac EGM signal, diagnose, and treat cardiac arrhythmias.

In some examples, medical device 16 includes communication circuitry 17 including any suitable circuitry, firmware, software, or any combination thereof for communicating with another device, such as external device 27 of FIG. 1. For example, communication circuitry 17 may include one or more processors, memory, wireless radios, antennae, transmitters, receivers, modulation and demodulation circuitry, filters, amplifiers, or the like for radio frequency communication with other devices, such as computing system 24. Medical device 16 may use communication circuitry 17 to receive downlinked data to control one or more operations of medical device 16 and/or send uplinked data to external device 27.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

While example system 10 of FIG. 1 depicts medical device 16, in other examples, the techniques of the disclosure may be applied to other types of medical devices that are not necessarily implantable. For example, a medical device in accordance with the techniques of the disclosure may include a wearable medical device or "smart" apparel worn by patient 14. For example, such a medical device may take the form of a wristwatch worn by patient 14 or circuitry that is adhesively affixed to patient 14. In another example, a medical device as described herein may include an external medical device with implantable electrodes.

In some examples, external device 27 takes the form of an external programmer or mobile device, such as a mobile phone, a "smart" phone, a laptop, a tablet computer, a personal digital assistant (PDA), etc. In some examples, external device 27 is a CareLink™ monitor available from Medtronic, Inc. A user, such as a physician, technician, surgeon, electro-physiologist, or other clinician, may interact with external device 27 to retrieve physiological or diagnostic information from medical device 16. A user, such as patient 14 or a clinician as described above, may also interact with external device 27 to program medical device 16, e.g., select or adjust values for operational parameters of medical device 16. External device 27 may include processing circuitry, a memory, a user interface, and communication circuitry capable of transmitting and receiving information to and from each of medical device 16 and computing system 24.

In some examples, computing system 24 takes the form of a handheld computing device, computer workstation, server or other networked computing device, smartphone, tablet, or external programmer that includes a user interface for presenting information to and receiving input from a user. In some examples, computing system 24 may include one or more devices that implement a machine learning system, such as a neural network, a deep learning system, or another type of machine learning system. A user, such as a physician, technician, surgeon, electro-physiologist, or other clinician, may interact with computing system 24 to retrieve physiological or diagnostic information from medical device 16. A user may also interact with computing system 24 to program medical device 16, e.g., select values for operational parameters of the IMD. Computing system 24 may include a processor configured to evaluate cardiac EGMs (or segments thereof) and/or other sensed signals transmitted from medical device 16 to computing system 24.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers and may thus form part of a large-scale public network infrastructure, e.g., the Internet. Network 25 may provide computing devices, such as computing system 24 and medical device 16, access to the Internet, and may provide a communication framework that allows the computing devices to communicate with one another. In some examples, network 25 may be a private network that provides a communication framework that allows computing system 24, medical device 16, and EMR database 66 to communicate with one another but isolates computing system 24, medical device 16, and EMR database 66 from external devices for security purposes. In some examples, the communications between computing system 24, medical device 16, and EMR database 66 are encrypted.

External device 27 and computing system 24 may communicate via wireless or non-wireless communication over network 25 using any techniques known in the art. In some examples, computing system 24 is a remote device that communicates with external device 27 via an intermediary device located in network 25, such as a local access point, wireless router, or gateway. While in the example of FIG. 1, external device 27 and computing system 24 communicate over network 25, in some examples, external device 27 and computing system 24 communicate with one another directly. Examples of communication techniques may include, for example, communication according to the Bluetooth® or BLE protocols. Other communication techniques are also contemplated. Computing system 24 may also communicate with one or more other external devices using a number of known communication techniques, both wired and wireless.

EMR database 66 stores EMR data for patient 14. EMR database 66 may include processing circuitry and one or more storage mediums (e.g., random access memory (RAM), read only memory (ROM), programmable read only memory (PROM), erasable programmable read only memory (EPROM), electronically erasable programmable read only memory (EEPROM), or flash memory. In some examples, EMR database 66 is a cloud computing system. In some examples, the functions of EMR database 66 are distributed across a number of computing systems.

In one example, computing system 24 receives patient data collected by medical device 16 of patient 14. In some examples, the patient data includes physiological data for patient 14, such as one or more of an activity level of patient 14, a heart rate of patient 14, a posture of patient 14, a cardiac electrogram of patient 14, a blood pressure of patient 14, a pulse transit time of patient 14, a respiration rate of patient 14, a hypopnea index or apnea of patient 14, accelerometer data for patient 14, features derived from accelerometer data of patient 14, such as activity counts, posture, statistical control process variables, etc., a raw electromyogram of patient 14, one or more features derived from a raw electromyogram or cardiac EGM of patient 14, such as heart rate variability, t-wave alternans, QRS morphology, etc., interval data and features derived from interval data, heart sounds, potassium levels, glycemic index, a temperature of patient 14, or any data derivable from the aforementioned parametric data, or any other types of patient parametric data. In some examples, medical device 16 or another device may automatically generate the patient parametric data by processing information from one or more sensors. For example, medical device 16 may determine, via one or more sensors, that patient 14 has fallen down, patient 14 is frail or suffers an illness, or that patient 14 is suffering an instance of sleep apnea.

In some examples, the patient data includes environmental data such as, air quality measurements, ozone levels, particulate counts, or pollution levels proximate to patient 14, an ambient temperature, or daylight hours. In some examples, one of medical device or external device 27 may sense, via one or more sensors, the environmental data. In another example, the environmental data is received by external device 27 via an application, such as a weather application, executing on external device 27, and uploaded to computing system 24 over network 25. In another example, computing system 24 collects the environmental data directly from a cloud service that has location-based data for patient 14.

In some examples, the patient data includes patient symptom data that is uploaded by patient 14 via an external device, such as external device 27. For example, patient 14 may upload the patient symptom data via an application executing on a smart phone. In some examples, patient 14 may upload the patient symptom data via a user interface (not depicted in FIG. 1), such as by touchscreen, keyboard, graphical user interface, voice commands, etc.

In some examples, the patient data includes device-related data, such as one or more of an impedance of one or more electrodes of the medical device, a selection of electrodes, a drug delivery schedule for the medical device, a history of electrical pacing therapy delivered to the patient, or diagnostic data for the medical device. In some examples, the medical device that collects the patient data is an IMD. In other examples, the medical device that collects the patient data is another type of patient device, such as a wearable medical device or a mobile device (e.g., a smartphone) of patient 14. In some examples, computing system 24 receives the patient data on a periodic, e.g., daily, basis.

In some examples, computing system 24 further receives EMR data for patient 14 from EMR database 66. The EMR data may be considered another form of patient data. In some examples, the EMR data stored by EMR database 66 may include many different types of historical medical information about patient 14. For example, EMR database 66 may store a medication history of the patient, a surgical procedure history of the patient, a hospitalization history of the patient, potassium levels of the patient over time, one or more lab test results for patient 14, a cardiovascular history of patient 14, or co-morbidities of patient 14 such as atrial fibrillation, heart failure, or diabetes, as examples.

Computing system 24 may implement a cardiac EGM monitoring system that may aid in the management of chronic cardiac disease. To implement the cardiac EGM monitoring system, computing system 24 may apply artificial intelligence (AI) techniques to analyze patient data, such as cardiac EGM data. Example AI techniques may include deep learning or other machine learning techniques. Neural network algorithms are one example of deep learning algorithms.

The AI techniques applied by medical device 16, external device 27, or computing system 24 may generate data regarding one or more aspects of the cardiac rhythm of patient 14. For instance, the AI techniques may identify occurrences of cardiac arrhythmias based at least in part on cardiac EGM strips obtained from one or more medical devices, such as medical device 16. A cardiac EGM strip comprises data representing a cardiac rhythm of a patient in a contiguous time period (e.g., 30 seconds, 45 seconds, etc.). A cardiac EGM strip may comprise a series of samples representing a waveform of the cardiac rhythm. A user (e.g., a technician, physician, patient, healthcare professional, or other type of user) may review the detected occurrences of the cardiac arrhythmias for diagnostic purposes or as part of performing ongoing care of patient 14. In addition to cardiac EGM strips, the AI techniques may use one or more other types of data to detect occurrences of cardiac arrhythmias, such as information from an electronic medical record of patient 14.

Signal processing techniques and heuristics applied to metrics extracted from processing cardiac EGM strips have previously been implemented in low power settings to detect cardiac arrhythmias, trigger recordings of EGM data, and for other purposes. The AI algorithms may augment or be used in place of such previously-implemented techniques. Advantageously, when using the AI algorithms, it may not be necessary to engineer features and signal processing techniques manually in order to identify occurrences of cardiac arrhythmias or other aspects of a cardiac rhythm of patient 14. Rather, the AI algorithms may have the ability to learn from population data and become representative models of how cardiac disease manifests in populations. The AI algorithms may be improved over time (e.g., by implementing strategies like reinforcement learning, residual learning, transfer learning, and so on).

The AI algorithms may be trained to identify one or more aspects of the cardiac rhythm of patient 14 that are of interest in a given cardiac EGM strip by applying a cardiac rhythm classification model that has been trained to identify such aspects of the cardiac rhythm of patient 14. The aspects of the cardiac rhythm of patient 14 may include various cardiac arrhythmias, locations of such cardiac arrhythmias within one or more cardiac EGM strips, which reflects the time of occurrence of the arrhythmia, morphological aspects of occurrences of cardiac arrhythmias, and so on. The cardiac rhythm classification model may be trained on EGM strips drawn from a population of subjects and, in some examples, other data.

This disclosure describes techniques for personalizing cardiac rhythm classification models. For instance, this disclosure describes techniques for training cardiac rhythm classification models for smaller cohorts of patients. This disclosure also describes techniques for training cardiac rhythm classification models for individual patients. Personalizing cardiac rhythm classification models may enable a user to analyze the cardiac EGM records of patient 14 in the context of a more representative population or relative to the previous history of patient 14. This may enable the user to make decisions more applicable to the individual patient in question. As described in detail elsewhere in this disclosure, such techniques may be used to reduce power consumption and/or bandwidth utilization of medical device 16 and/or external device 27.

Thus, in one example of this disclosure, an AI system may obtain a cardiac EGM strip for patient 14 (i.e., a current patient). The AI system is a computing system that comprises a memory and one or more processing circuits. In the context of FIG. 1, the AI system may be medical device 16, computing system 24, external device 27, or another device or system of devices. Thus, in this disclosure, discussion of actions performed by the AI system may apply to actions performed by any of these devices, unless otherwise indicated.

Additionally, the AI system may apply a first cardiac rhythm classifier (CRC) with a segment of the cardiac EGM strip as input. A CRC is an example of a cardiac rhythm classification model, which may be implemented as a neural network or other type of deep learning technology. The segment of the cardiac EGM strip may include all of the cardiac EGM strip or a subsegment of the cardiac EGM strip. In some examples, the input to the CRC includes data in addition to the segment of the cardiac EGM strip, such as data in EMR database 66.

The first CRC is trained on training cardiac EGM strips from a first population. The first population includes a plurality of patients. In some examples, the first population includes all patients whose cardiac EGM data is being monitored by computing system 24 or a subpopulation thereof. In some instances where computing system 24 implements a global or regional monitoring system, the first population may include many thousands or even millions of patients. Because the first CRC is trained using such a population, this disclosure may refer to the first CRC as the generalized CRC. Training a CRC based on cardiac EGM strips may apply to training the CRC based on segments of the cardiac EGM strips.

When the AI system applies the first CRC to the segment of the cardiac EGM strip, the first CRC generates, based on the segment of the cardiac EGM strip, first data regarding an aspect of a cardiac rhythm of patient 14. For example, the first CRC may be implemented as a neural network having an input layer, an output layer, and one or more hidden layers between the input layer and the output layer. The input layer may include an input neuron for each sample value of the segment of the cardiac EGM strip. The output layer may include an output neuron corresponding to each cardiac arrhythmia in a set of one or more cardiac arrhythmias. When the AI system applies the first CRC to the segment of the cardiac EGM strip, the input neurons receive the sample values from the segment, the hidden layers process the sample values, and the output neurons may output values indicating whether or not the segment represents an occurrence of the corresponding cardiac arrhythmia.

Furthermore, in this example, the AI system may apply a second CRC with the segment of the cardiac EGM strip as input. The second CRC is a version of the first CRC that is trained on training cardiac EGM strips from a second population. The second population is smaller than the first population. For instance, in some examples, the second population may consist only of patient 14. In other examples, the second population may be a cohort of patients who share one or more characteristics with patient 14. Such characteristics may include diagnostic or procedure codes, implanted medical devices, age, sex, tobacco use, comorbidities, gender, size, and so on. In some examples, the first population includes the second population. In other examples, the first population does not include the second population. Because the second CRC is trained using a smaller population than the first population, this disclosure may refer to the second CRC as a specialized CRC. When the AI system applies the specialized CRC to the segment of the cardiac EGM strip, the specialized CRC generates, based on the segment of the cardiac EGM strip, second data regarding the aspect of the cardiac rhythm type.

Aside from being trained using different training data, the specialized CRC may be implemented in the same manner as the generalized CRC. For instance, in an example where the generalized CRC and the specialized CRC are implemented as neural networks, the generalized CRC and the specialized CRC may have the same number and arrangement of neurons. However, in this example, parameters (e.g., weights of inputs to neurons, bias values, etc.) of the neural networks of the generalized CRC and the specialized CRC may differ. In other examples, the specialized CRC may be implemented in a different manner from the generalized CRC. For instance, the specialized CRC may include more or fewer layers, neurons, etc. than the generalized CRC.

The AI system may generate output data based on the first data and/or the second data. The AI system may generate the output data in one or more of various ways. For instance, the AI system may generate output data in the form of graphs, charts, lists, tables, or other arrangements of data that enable a user (e.g., the patient, physician, health monitoring technician, family member, etc.) to review and/or compare one or more types of data regarding one or more aspects of a cardiac rhythm of patient 14. For instance, in one such example where the first data comprises an indication of whether the segment of the cardiac EGM strip represents an occurrence of a cardiac arrhythmia and the second data comprises an indication of whether the segment of the cardiac EGM strip represents an occurrence of the cardiac arrhythmia, the AI system may collect and process such indications to generate a bar chart that compares the number of occurrences of the cardiac arrhythmia identified by the generalized CRC and the number of occurrences of the cardiac arrhythmia identified by the specialized CRC.

In some examples where the AI system is implemented on medical device 16, medical device 16 may send the cardiac EGM strip to external device 27 when the generalized CRC determines that a segment of the cardiac EGM strip represents an occurrence of a cardiac arrhythmia. In some examples, external device 27 may then send the cardiac EGM strip to computing system 24 via network 25. Thus, the cardiac EGM strip may be available for review and further processing by computing system 24, external device 27, and/or users thereof. However, because the generalized CRC is trained based on the first population and not trained specifically to patient 14, the generalized CRC may under-identify occurrences of the cardiac arrhythmia in segments of cardiac EGM strips from patient 14 as compared to the specialized CRC. Thus, if medical device 16 were only to apply the generalized CRC, medical device 16 might not send cardiac EGM strips to external device 27, despite the cardiac EGM strips potentially representing occurrences of the cardiac arrhythmia. However, in this example, by applying the specialized CRC, medical device 16 may identify additional cardiac EGM strips that may represent occurrences of the cardiac arrhythmia. Medical device 16 may then send the additional cardiac EGM strips to external device 27. This process may conserve power at medical device 16 and may conserve network bandwidth because it may obviate the need for transmitting all cardiac EGM strips in order for external device 27 and/or computing system 24 to access cardiac EGM strips that represent occurrences of the cardiac arrhythmia that were not identified by the generalized CRC. Similar considerations may apply in examples where the AI system is implemented by external device 27 and external device 27 transmits cardiac EGM strips to computing system 24.

In some examples where the AI system is implemented at medical device 16, the generalized CRC may over-identify occurrences of the cardiac arrhythmia in segments of cardiac EGM strips from patient 14 as compared to the specialized CRC. Hence, in one such example, medical device 16 may, in one configuration, transmit a cardiac EGM strip to external device 27 only when both the generalized CRC and the specialized CRC determine that the cardiac EGM strip represents an occurrence of the cardiac arrhythmia. This may reduce the amount of data transmitted by medical device 16, thereby conserving power and reducing bandwidth consumption. Similar considerations may apply in examples where the AI system is implemented by external device 27 and external device 27 transmits cardiac EGM strips to computing system 24.

Furthermore, in some examples, the AI system is implemented at medical device 16 and external device 27. For instance, in this example, medical device 16 may implement the generalized CRC. In this example, medical device 16 may transmit to external device 27 cardiac EGM strips determined by the generalized CRC to represent occurrence of a cardiac arrhythmia. Furthermore, in this example, external device 27 may apply the specialized CRC to the cardiac EGM strips received from medical device 16. In this example, external device 27 may, in some modes, transmit to computing system 24 those ones of the received cardiac EGM strips that were determined by the specialized CRC to represent occurrences of the cardiac arrhythmia. This may reduce the bandwidth consumption associated with transmitting cardiac EGM strips to computing system 24 via network 25.

Figure 2:
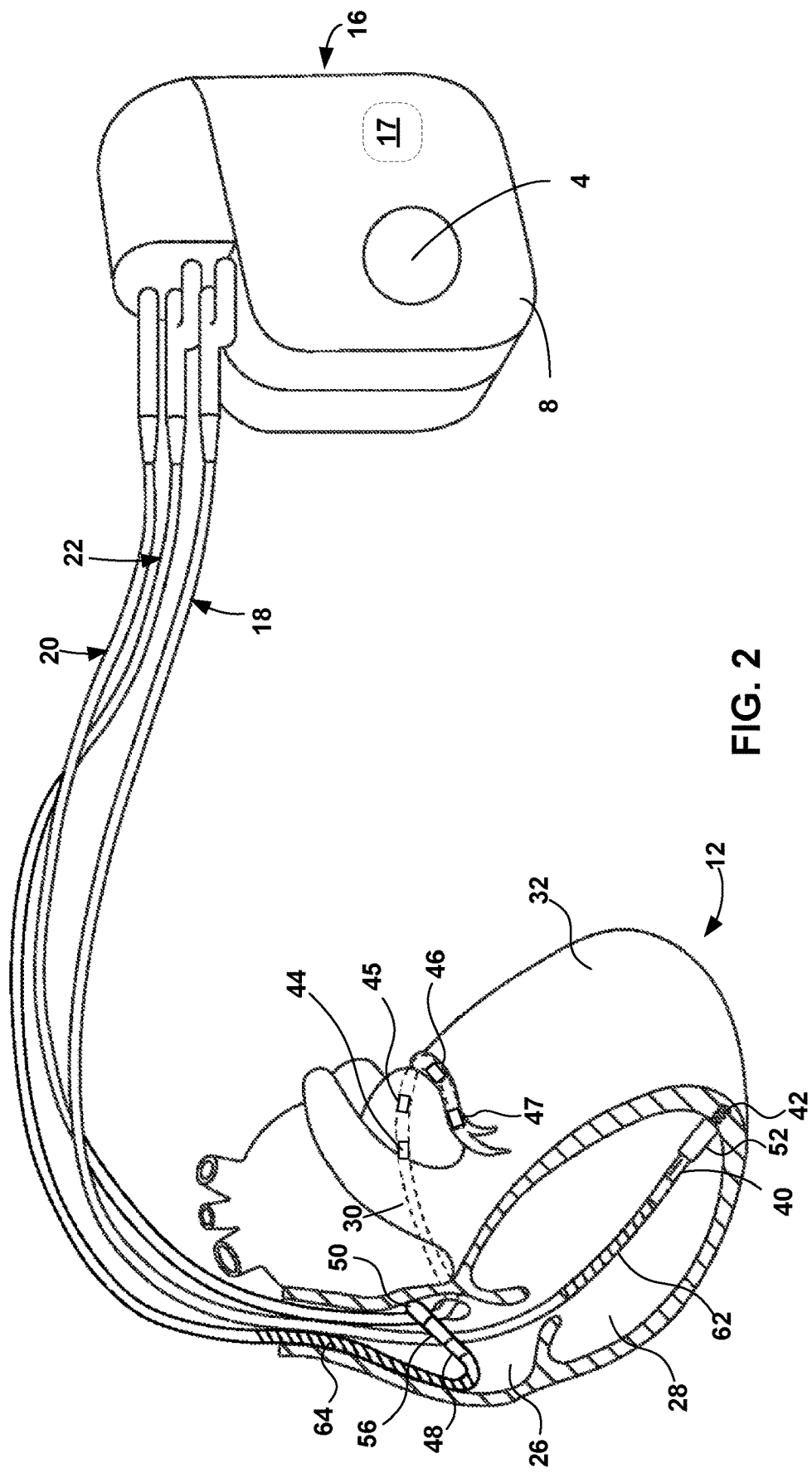
FIG. 2 is a conceptual diagram illustrating an implantable medical device (IMD) and leads of the system of FIG. 1 in greater detail.

FIG. 2 is a conceptual diagram illustrating medical device 16 and leads 18, 20, 22 of system 10 of FIG. 1 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 comprises segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40 and 44-48 take the form of ring electrodes, and electrodes 42 and 50 may take the form of extendable helix tip electrodes mounted retractably within insulative electrode heads 53 and 56, respectively. Leads 18 and 22 also include elongated electrodes 62 and 64, respectively, which may take the form of a coil. In some examples, each of electrodes 40, 42, 44-48, 50, 62, and 64 is electrically coupled to a respective conductor within the lead body of its associated lead 18, 20, 22 and thereby coupled to circuitry within medical device 16.

In some examples, medical device 16 includes one or more housing electrodes, such as housing electrode 4 illustrated in FIG. 2, which may be formed integrally with an outer surface of hermetically-sealed housing 8 of medical device 16 or otherwise coupled to housing 8. In some examples, housing electrode 4 is defined by an uninsulated portion of an outward facing portion of housing 8 of medical device 16. Other divisions between insulated and uninsulated portions of housing 8 may be employed to define two or more housing electrodes. In some examples, a housing electrode comprises substantially all of housing 8.

Housing 8 encloses signal generation circuitry that generates therapeutic stimulation, such as cardiac pacing, cardioversion, and defibrillation pulses, as well as sensing circuitry for sensing electrical signals attendant to the depolarization and repolarization of heart 12. Housing 8 may also enclose a memory for storing the sensed electrical signals. Housing 8 may also enclose communication circuitry 17 for communication between medical device 16 and computing system 24.

Medical device 16 senses electrical signals attendant to the depolarization and repolarization of heart 12 via electrodes 4, 40, 42, 44-48, 50, 62, and 64. Medical device 16 may sense such electrical signals via any bipolar combination of electrodes 40, 42, 44-48, 50, 62, and 64. Furthermore, any of the electrodes 40, 42, 44-48, 50, 62, and 64 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or extravascular (e.g., subcutaneous or substernal) leads not positioned within heart 12.

Medical device 16 may send patient data to computing system 24 (e.g., by way of external device 27). The patient data may include data based on the electrical signals detected by electrodes 4, 40, 42, 44-48, 50, 62, and/or 64. For example, medical device 16 may gather and send cardiac EGM data to computing system 24. In accordance with the techniques of this disclosure, computing system 24 may use the patient data to determine probability values that indicate probabilities that patient 14 has experienced occurrences of one or more cardiac arrhythmias.

Although described herein in the context of an example medical device 16 that provides therapeutic electrical stimulation, the techniques disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin, Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Figure 3:
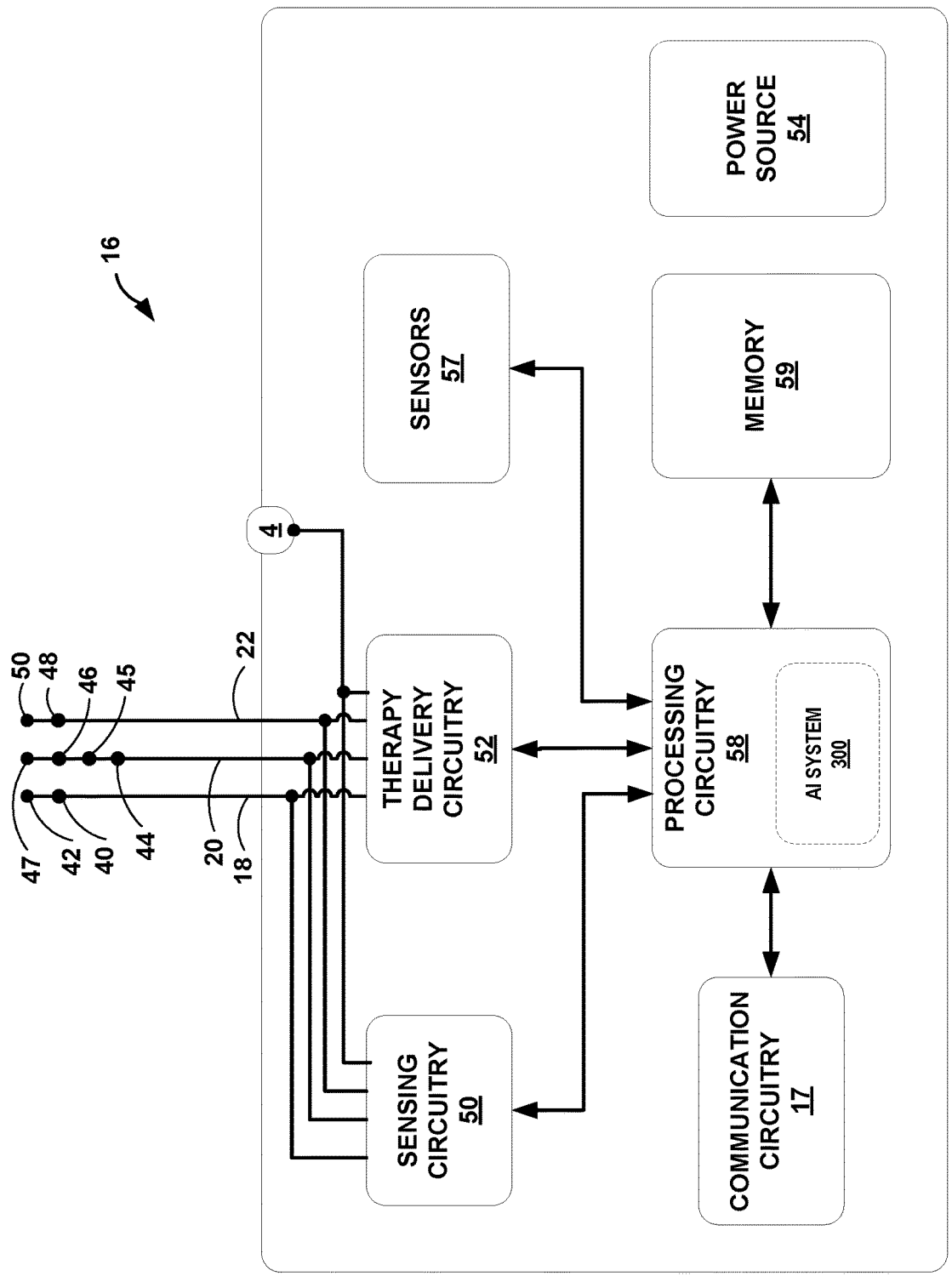
FIG. 3 is a block diagram of an example implantable medical device according to the techniques of the disclosure.

FIG. 3 is a block diagram of example medical device 16 according to the techniques of the disclosure. In the illustrated example, medical device 16 includes processing circuitry 58, memory 59, communication circuitry 17, sensing circuitry 50, therapy delivery circuitry 52, sensors 57, and power source 54. Memory 59 includes computer-readable instructions that, when executed by processing circuitry 58, cause medical device 16 and processing circuitry 58 to perform various functions attributed to medical device 16 and processing circuitry 58 herein (e.g., performing short-term prediction of cardiac arrhythmias, delivering therapy, such as anti-tachycardia pacing, bradycardia pacing, and post-shock pacing therapy, etc.). Memory 59 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 58 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 58 may include multiple components, such as any combination of one or more microprocessors, one or more controllers, one or more DSPs, one or more ASICs, or one or more FPGAs, as well as other discrete or integrated logic circuitry. The functions attributed to processing circuitry 58 herein may be embodied as software, firmware, hardware or any combination thereof.

Processing circuitry 58 controls therapy delivery circuitry 52 to deliver stimulation therapy to heart 5 according to therapy parameters, which may be stored in memory 59. For example, processing circuitry 58 may control therapy delivery circuitry 52 to deliver electrical pulses with the amplitudes, pulse widths, frequency, or electrode polarities specified by the therapy parameters. In this manner, therapy delivery circuitry 52 may deliver pacing pulses (e.g., ATP pulses, bradycardia pacing pulses, or post-shock pacing therapy) to heart 5 via electrodes 34 and 40. In some examples, therapy delivery circuitry 52 may deliver pacing stimulation, e.g., ATP therapy, bradycardia therapy, or post-shock pacing therapy, in the form of voltage or current electrical pulses. In other examples, therapy delivery circuitry 52 may deliver one or more of these types of stimulation in the form of other signals, such as sine waves, square waves, or other substantially continuous time signals.

Therapy delivery circuitry 52 is electrically coupled to electrodes 34 and 40 carried on the housing of medical device 16. Although medical device 16 may only include two electrodes, e.g., electrodes 34 and 40, in other examples, medical device 16 may utilize three or more electrodes. Medical device 16 may use any combination of electrodes to deliver therapy and/or detect electrical signals from patient 14. In some examples, therapy delivery circuitry 52 includes a charging circuit, one or more pulse generators, capacitors, transformers, switching modules, and/or other components capable of generating and/or storing energy to deliver as pacing therapy, cardiac resynchronization therapy, other therapy or a combination of therapies. In some examples, therapy delivery circuitry 52 delivers therapy as one or more electrical pulses according to one or more therapy parameter sets defining an amplitude, a frequency, a voltage or current of the therapy, or other parameters of the therapy.

Sensing circuitry 50 monitors signals from one or more combinations (also referred to as vectors) of two or more electrodes from among electrodes 4, 40, 42, 44-48, 50, 62 (FIG. 2), and 64 (FIG. 2) in order to monitor electrical activity of heart 12, impedance, or other electrical phenomenon. In some examples, sensing circuitry 50 includes one or more analog components, digital components or a combination thereof. In some examples, sensing circuitry 50 includes one or more sense amplifiers, comparators, filters, rectifiers, threshold detectors, analog-to-digital converters (ADCs) or the like. In some examples, sensing circuitry 50 converts sensed signals to digital form and provides the digital signals to processing circuitry 58 for processing or analysis. In one example, sensing circuitry 50 amplifies signals from electrodes 4, 40, 42, 44-48, 50, 62, and 64 and converts the amplified signals to multi-bit digital signals by an ADC.

In some examples, sensing circuitry 50 performs sensing of the cardiac electrogram to determine heart rates or heart rate variability, or to detect arrhythmias (e.g., tachyarrhythmias or bradycardia) or to sense other parameters or events from the cardiac electrogram. Sensing circuitry 50 may also include switching circuitry to select which of the available electrodes (and the electrode polarity) are used to sense the heart activity, depending upon which electrode combination, or electrode vector, is used in the current sensing configuration. Processing circuitry 58 may control the switching circuitry to select the electrodes that function as sense electrodes and their polarity. Sensing circuitry 50 may include one or more detection channels, each of which may be coupled to a selected electrode configuration for detection of cardiac signals via that electrode configuration. In some examples, sensing circuitry 50 compares processed signals to a threshold to detect the existence of atrial or ventricular depolarizations and indicate the existence of the atrial depolarization (e.g., P-waves) or ventricular depolarizations (e.g., R-waves) to processing circuitry 58. Sensing circuitry 50 may comprise one or more amplifiers or other circuitry for comparison of the cardiac electrogram amplitude to a threshold, which may be adjustable.

Processing circuitry 58 may include a timing and control module, which may be embodied as hardware, firmware, software, or any combination thereof. The timing and control module may comprise a dedicated hardware circuit, such as an ASIC, separate from other processing circuitry 58 components, such as a microprocessor, or a software module executed by a component of processing circuitry 58, which may be a microprocessor or ASIC. The timing and control module may implement programmable counters. If medical device 16 is configured to generate and deliver bradycardia pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

In some examples, processing circuitry 58 of medical device 16 implements AI system 300. For instance, processing circuitry 58 may apply a generalized CRC and/or a specialized CRC to cardiac EGM strips, as described elsewhere in this disclosure. Processing circuitry 58 may implement AI system 300 using special-purpose circuitry or by executing software instructions stored on a computer-readable medium, such as memory 59. Sensing circuitry 50 may generate cardiac EGM strips based on data received from electrodes 4, 40, 42, 44-48, 50, 62, and 64. Communication circuitry 17 may transmit cardiac EGM strips and/or other data to external device 27.

Memory 59 may be configured to store a variety of operational parameters, therapy parameters, sensed and detected data, and any other information related to the therapy and treatment of patient 14. In the example of FIG. 3, memory 59 may store sensed cardiac EGMs, e.g., associated with detected or predicted arrhythmias, and therapy parameters that define the delivery of therapy provided by therapy delivery circuitry 52. In other examples, memory 59 may act as a temporary buffer for storing data until it can be uploaded to computing system 24.

Communication circuitry 17 includes any suitable circuitry, firmware, software, or any combination thereof for communicating with another device, such as computing system 24 via network 25 of FIG. 1. For example, communication circuitry 17 may include one or more antennae, modulation and demodulation circuitry, filters, amplifiers, or the like for radio frequency communication with other devices, such as computing system 24 via network 25. Under the control of processing circuitry 58, communication circuitry 17 may receive downlink telemetry from and send uplink telemetry to computing system 24 with the aid of an antenna, which may be internal and/or external. Processing circuitry 58 may provide the data to be uplinked to computing system 24 and the control signals for the telemetry circuit within communication circuitry 17, e.g., via an address/data bus. In some examples, communication circuitry 17 may provide received data to processing circuitry 58 via a multiplexer.

Power source 54 may be any type of device that is configured to hold a charge to operate the circuitry of medical device 16. Power source 54 may be provided as a rechargeable or non-rechargeable battery. In other example, power source 54 may incorporate an energy scavenging system that stores electrical energy from movement of medical device 16 within patient 14.

In accordance with the techniques of the disclosure, medical device 16 collects, via sensing circuitry 50 and/or sensors 57, patient data of patient 14. Sensors 57 may include one or more sensors, such as one or more accelerometers, pressure sensors, optical sensors for O2 saturation, etc. In some examples, the patient data includes one or more of an activity level of patient 14, a heart rate of patient 14, a posture of patient 14, a cardiac electrogram of patient 14 (e.g., cardiac EGM strips of patient 14), a blood pressure of patient 14, accelerometer data for patient 14, or other types of patient parametric data. Medical device 16 uploads, via communication circuitry 17, the patient parametric data to computing system 24 over network 25. In some examples, medical device 16 uploads the patient parametric data to computing system 24 on a daily basis. In some examples, the patient parametric data includes one or more values that represent average measurements of patient 14 over a long-term time period (e.g., about 24 hours to about 48 hours). For example, one or more other devices, such as a wearable medical device or a mobile device (e.g., a smartphone) of patient 14, may collect the patient parametric data and upload the patient parametric data to external device 27 and/or computing system 24.

Although described herein in the context of example medical device 16 that provides therapeutic electrical stimulation, the techniques for short-term prediction of cardiac arrhythmia disclosed herein may be used with other types of devices. For example, the techniques may be implemented with a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Figure 4:
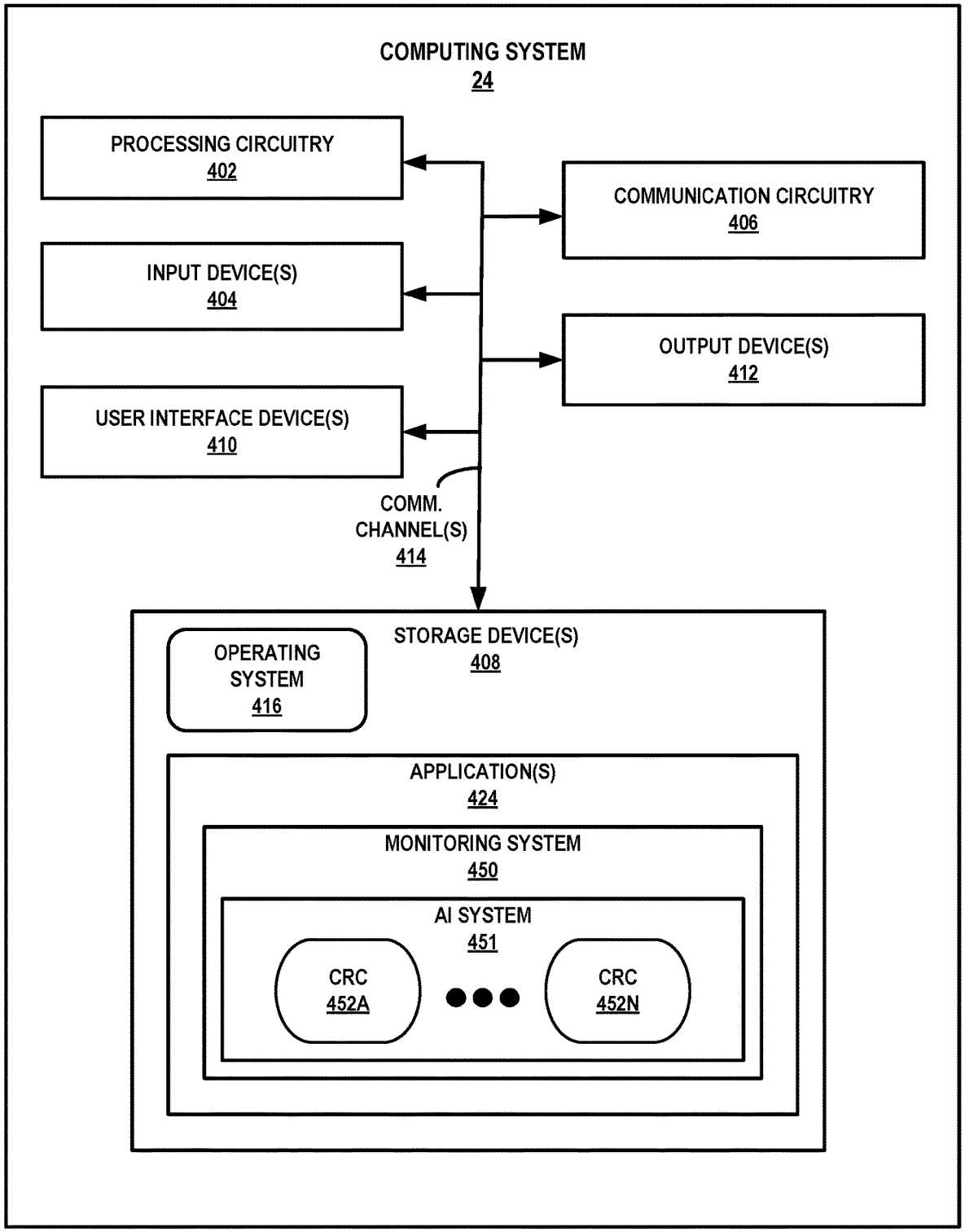
FIG. 4 is a block diagram illustrating an example computing device that operates in accordance with one or more techniques of the present disclosure.

FIG. 4 is a block diagram illustrating an example computing system 24 that operates in accordance with one or more techniques of the present disclosure. In one example, computing system 24 includes processing circuitry 402 for executing applications 424 that include monitoring system 450 or any other applications described herein. Although shown in FIG. 4 as a stand-alone computing system 24 for purposes of example, computing system 24 may be any component or system that includes processing circuitry or other suitable computing environment for executing software instructions and, for example, need not necessarily include one or more elements shown in FIG. 4 (e.g., communication circuitry 406; and in some examples components such as storage device(s) 408 may not be co-located or in the same chassis as other components). In some examples, computing system 24 may be a cloud computing system distributed across a plurality of devices.

As shown in the example of FIG. 4, computing system 24 includes processing circuitry 402, one or more input devices 404, communication circuitry 406, one or more output devices 412, one or more storage devices 408, and user interface (UI) device(s) 410. Computing system 24, in one example, further includes one or more application(s) 424 such as monitoring system 450, and operating system 416 that are executable by computing system 24. Each of components 402, 404, 406, 408, 410, and 412 are coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within computing system 24. For example, processing circuitry 402 may be capable of processing instructions stored in storage device 408. Examples of processing circuitry 402 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within computing system 24 during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include random access memories (RAM), dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on computing system 24 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing system 24, in some examples, also includes communication circuitry 406. Computing system 24, in one example, utilizes communication circuitry 406 to communicate with external devices, such as medical device 16 and EMR database 66 of FIG. 1.

Communication circuitry 406 may include a network interface card, such as an Ethernet card, an optical transceiver, a radio frequency transceiver, or any other type of device that can send and receive information. Other examples of such network interfaces may include 3G, 4G, 5G, and WI-FI™ radios.

Computing system 24, in one example, also includes one or more user interface devices 410. User interface devices 410, in some examples, are configured to receive input from a user through tactile, audio, or video feedback. Examples of user interface devices(s) 410 include a presence-sensitive display, a mouse, a keyboard, a voice responsive system, video camera, microphone or any other type of device for detecting a command from a user. In some examples, a presence-sensitive display includes a touch-sensitive screen.

One or more output devices 412 may also be included in computing system 24. Output device 412, in some examples, is configured to provide output to a user using tactile, audio, or video stimuli. Output device 412, in one example, includes a presence-sensitive display, a sound card, a video graphics adapter card, or any other type of device for converting a signal into an appropriate form understandable to humans or machines. In some examples, output device(s) 412 include a display device. Additional examples of output device 412 include a speaker, a cathode ray tube (CRT) monitor, a liquid crystal display (LCD), or any other type of device that can generate intelligible output to a user.

Computing system 24 may include operating system 416. Operating system 416, in some examples, controls the operation of components of computing system 24. For example, operating system 416, in one example, facilitates the communication of one or more applications 424 and monitoring system 450 with processing circuitry 402, communication circuitry 406, storage device 408, input device 404, user interface devices 410, and output device 412.

Application 422 may also include program instructions and/or data that are executable by computing system 24. Example application(s) 422 executable by computing system 24 may include monitoring system 450. Other additional applications not shown may alternatively or additionally be included to provide other functionality described herein and are not depicted for the sake of simplicity.

In accordance with the techniques of the disclosure, applications 424 include a monitoring system 450. Monitoring system 450 may be configured to receive patient data, evaluate the patient data, and generate output data. For instance, in one example, monitoring system 450 may generate notifications when monitoring system 450 determines that it is likely that patient 14 (FIG. 1) has experienced one or more cardiac arrhythmia events that belong to one or more cardiac arrhythmias. In another example, monitoring system 450 may generate one or more charts showing changes to one or more aspects of the cardiac rhythm of patient 14.

As shown in the example of FIG. 4, monitoring system 450 may, in some examples, implement an AI system 451 that includes one or more CRCs. For instance, in the example of FIG. 4, monitoring system 450 may include CRCs 452A through CRC 452N (collectively, "CRCs 452").

CRCs 452 may include a generalized CRC and one or more specialized CRCs. Although the following discussion of CRCs refers to CRCs 452 and AI system 451, the following discussion may apply equally to CRCs and AI systems implemented in devices or systems other than computing system 24, such as in medical device 16 or external device 27 or a combination thereof.

In some examples, each of CRCs 452 is implemented using one or more neural network systems, deep learning systems, or other type of supervised or unsupervised machine learning systems. For example, a CRC may be implemented by a feedforward neural network, such as a convolutional neural network, a radial basis function neural network, a recurrent neural network, a modular or associative neural network. In some examples, AI system 451 trains CRCs 452 with patient data, including cardiac EGM strips, for different populations of patients to data regarding one or more aspects of a cardiac rhythm of the patients in the populations. In some examples, after AI system 451 has pre-trained a CRC with patient data for a population of patients, AI system 451 may further train the machine learning model with patient data specific to patient 14 or a smaller cohort of patients.

In some examples, AI system 451 trains a CRC with the patient data for a population of patients, determines an error rate of the CRC, and then feeds the error rate back to the CRC so as to allow the CRC to update its predictions based on the error rate. In some examples, the error rate may correspond to differences between output data determined by the CRC based on input data and prelabeled output data for the same input data. In some examples, AI system 451 may use an error function to determine the error rate. The error function may be implemented using signal processing techniques and heuristics in the manner conventionally used to detect occurrences of cardiac arrhythmias. In some examples, monitoring system 450 may receive, from a user (e.g., patient 14, a clinician, or another type of person) feedback indicating whether a detected cardiac arrhythmia occurred in patient 14 within a particular time period. In some examples, monitoring system 450 may receive, from medical device 16, a message indicating that medical device 16 has detected (or has not detected) an occurrence of a cardiac arrhythmia in patient 14. In some examples, monitoring system 450 may obtain the feedback in other ways, such as by periodically checking the EMR data to determine if a cardiac arrhythmia occurred. Monitoring system 450 may update the CRC with the feedback. Thus, the training process may occur iteratively so as to incrementally improve the data generated by the CRC by "learning" from correct and incorrect data generated by the CRC in the past. Further, the training process may be used to further fine-tune a CRC that is trained using population-based data to generate more accurate data for a particular individual. In some examples, personnel of a monitoring service may provide the feedback.

In some examples, each of CRCs 452 is implemented using a neural network. The neural network may include an input layer, and output layer, and one or more hidden layers between the input layer and the output layer. Each layer of the neural network includes one or more artificial neurons, which this disclosure refers to simply as neurons. The input layer of the neural network includes a plurality of input neurons. The input layer may include a separate input neuron for each sample value of a segment of a cardiac EGM strip. In some examples, the segment may be coterminous with the cardiac EGM strip. In other examples, the segment may be subsegment of the cardiac EGM strip. For instance, in an example where the cardiac EGM strip comprises samples representing 45 seconds of a cardiac rhythm of patient 14, the segment may comprise samples representing the first 10 seconds of the cardiac EGM strip.

AI system 451 may provide overlapping segments of cardiac EGM strips to a CRC. For example, AI system 451 may provide a segment comprising samples representing seconds 0 through 10 of a cardiac EGM strip, then provide a segment comprising samples representing seconds 5 through 15 of the cardiac EGM strip, then provide a segment comprising samples representing seconds 10 through 20 of the cardiac EGM strip, and so on. In some examples, computing system 24 may provide a segment that spans two or more cardiac EGM strips.

In some examples, each of CRCs 452 is a convolutional neural network (CNN). For instance, in one example, a convolutional layer may follow an input layer of the type described above. A first convolutional layer neuron may receive input from a first set of input layer neurons consisting of a given number of consecutive input layer neurons; a second convolutional layer neuron may receive input from a second set of input layer neurons consisting of the same given number of consecutive input layer neurons, but offset from the first input layer neuron of the first set of input layer neurons by a stride length; a third convolutional layer neuron may receive input from a third set of input layer neurons consisting of the same given number of consecutive input layer neurons, but offset from the first input layer neuron of the second set of input layer neurons by the stride length; and so on. The given number of consecutive input neurons and the stride length are different hyperparameters of the CNN. One or more fully connected hidden layers may follow the convolutional layer. Implementing CRCs 452 as CNNs may increase performance of CRCs 452.

In some examples of this disclosure, for each respective cardiac arrhythmia of a set of one or more cardiac arrhythmias, each of CRCs 452 may generate data that indicate whether one or more occurrences of the respective cardiac arrhythmia are represented in a segment of a cardiac EGM strip. For instance, in one example, a hidden layer of the CRC provides input data to the output layer of CRC. For each respective cardiac arrhythmia of the set of cardiac arrhythmias, the output layer of the CRC that includes a separate output neuron corresponding to the respective cardiac arrhythmia. The output neuron corresponding to the respective cardiac arrhythmia receives input data from a single neuron in the hidden layer of the CRC that also corresponds to the respective cardiac arrhythmia. The data generated by the hidden layer neuron corresponding to the respective cardiac arrhythmia comprises a probability value indicating a probability that an occurrence of the cardiac arrhythmia has occurred in the segment of the cardiac EGM strip. An activation function of the output neurons may apply a thresholding function to the probability values generated by the hidden layer neurons. For each output neuron, the thresholding function may cause the output neuron to generate a first value (e.g., 1) if the probability value provided to the output neuron is greater than a threshold and to generate a second value (e.g., 0) if the probability value provided to the output neuron is less than the same threshold.

Furthermore, in the example of the previous paragraph, AI system 451 may use the probability values generated by the hidden layer to track where occurrences of cardiac arrhythmias occurred within a cardiac EGM strip. For instance, as mentioned above, a cardiac EGM strip may be subdivided into segments and AI system 451 provides the segments to CRCs 452 as input. Thus, by determining which segment of the cardiac EGM strip resulted in a highest probability values corresponding to a cardiac arrhythmia, AI system 451 may determine which segment most likely represents the occurrence of the cardiac arrhythmia.

As noted elsewhere in this disclosure, the input provided to CRCs 452 may include patient data in addition to segments of cardiac EGM strips. For instance, in some examples, the patient data may additionally include data regarding the patient's physiological status (e.g., patient physiological statuses such as activity, posture, respiration, etc.), which may also be captured by medical device 16. Patient data corresponding to different physiological conditions (e.g., rest, resting at night, resting at night with high posture angle etc.) can be used as additional parameters for model training or input data for CRCs 452. Using such data may enable the AI system to detect occurrences of a cardiac arrhythmia during other disease conditions (e.g., a sensitive model for tachycardia during rest can be used to monitor heart failure (HF) patients; a model for bradycardia during activity can be used to monitor patients for chronotropic incompetence). In some examples, monitoring system 450 receives, via communication circuitry 406, EMR data for patient 14 from EMR database 66. In some examples, the EMR data stored by EMR database 66 may include many different types of historical medical information about patient 14. For example, EMR database 66 may store a medication history of the patient, a surgical procedure history of the patient, a hospitalization history of the patient, potassium levels of the patient over time, or one or more lab test results for the patient, etc. The EMR data may form part of the patient data used as input to one or more of CRCs 452.

In some examples, each of CRCs 452 converts the patient data into one or more vectors and tensors (e.g., multi-dimensional arrays) that represent the patient data. CRCs 452 may apply mathematical operations to the one or more vectors and tensors to generate a mathematical representation of the patient data. CRCs 452 may determine different weights that correspond to identified relationships between the patient data and the occurrence of the cardiac arrhythmia. CRCs 452 may apply the different weights to the patient data to generate the probability values.

Figure 5:
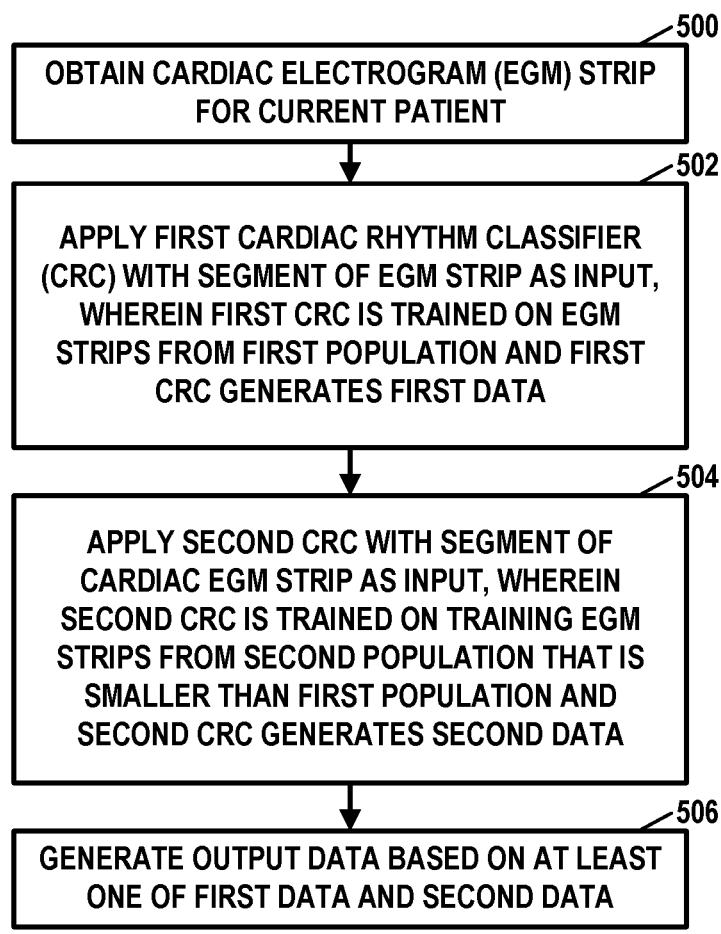
FIG. 5 is a flowchart illustrating an example operation in accordance with the techniques of the disclosure.

FIG. 5 is a flowchart illustrating an example operation in accordance with the techniques of the disclosure. For convenience, FIG. 5 is described with respect to FIG. 1. The flowcharts of this disclosure are presented as examples. Other examples in accordance with techniques of this disclosure may include more, fewer, or different actions, or actions may be performed in different orders or in parallel. The operation of FIG. 5 may be performed by an AI system implemented on one or more of medical device 16, computing system 24, external device 27, and/or other devices.

In the example of FIG. 5, the AI system may obtain a cardiac EGM strip for patient 14 (i.e., a current patient) (500). The AI system may obtain the cardiac EGM strip for the patient 14 in one or more of various ways. For instance, in an example where computing system 24 implements the AI system, computing system 24 may obtain the cardiac EGM strip for patient 14 from medical device 16 (e.g., by way of external device 27 and network 25). In some examples where the AI system is implemented in medical device 16, the AI system may obtain the cardiac EGM strip by generating the cardiac EGM strip based on data from electrodes. In some examples, the AI system may obtain the cardiac EGM strip for the current patient from a database (e.g., EMR database 66) that stores one or more cardiac EGM strips for the current patient. Other examples of obtaining cardiac EGM strips are described elsewhere in this disclosure.

Furthermore, in the example of FIG. 5, the AI system may apply a first CRC (i.e., a generalized CRC) with a segment of the cardiac EGM strip as input (502). The first CRC is trained on training cardiac EGM strips from a first population. In some examples, the first population includes all patients whose cardiac EGM data is being monitored by computing system 24. When the AI system applies the first CRC, the first CRC generates, based on the segment of the cardiac EGM strip, first data regarding an aspect of a cardiac rhythm of patient 14.

In some examples, the aspect of the cardiac rhythm of the current patient is an occurrence of an occurrence of a cardiac arrhythmia in the cardiac rhythm of the current patient. In such examples, the first data may include data indicating whether the segment of the cardiac EGM strip represents one or more occurrences of one or more cardiac arrhythmias. For instance, the first data may be based on a first probability that the segment of the cardiac EGM strip represents at least one occurrence of the cardiac arrhythmia. In some examples, for each cardiac arrhythmia of a set of one or more cardiac arrhythmias, the first data may include a confidence value that indicates a level of confidence that an occurrence of the cardiac arrhythmia is represented in the cardiac EGM strip. The confidence values may be output values of neurons in a hidden layer preceding the output layer. In some examples, the first output data may include timing data that indicate where occurrences of one or more cardiac arrhythmias occurred in the cardiac EGM strip.

Additionally, the AI system may apply a second CRC (i.e., a specialized CRC) with the segment of the cardiac EGM strip as input (504). The second CRC is a version of the first CRC that is trained on the training cardiac EGM strips from a second population that is smaller than the first population. For instance, in some examples, the second population may consist only of patient 14. In other examples, the second population may be a cohort of patients, such as a cohort of patients who share one or more characteristics with patient 14. Example characteristics may include a diagnosis of the cohort of patients and patient 14. When the AI system applies the second CRC, the second CRC may generate, based on the segment of the cardiac EGM strip, second data regarding the cardiac rhythm type. The second data may include the same types of data as the first data. For instance, the second data is based on a second probability that the segment of the cardiac EGM strip represents at least one occurrence of the cardiac arrhythmia.

The AI system may generate output data based on at least one of the first data and the second data (506). In some examples, computing system 24 may present the output data via a graphical user interface, a voice interface, a webpage, or in another form. In some examples, the output data may comprise a notification or message, such as an email message, a text message, an in-app notification, an instant message, voicemail message, or another type of message.

In some examples, the AI system may output a dashboard interface for display. The dashboard interface is a type of graphical user interface that includes the output data. The dashboard interface may include lists, charts, sparklines, bar graphs, tables, or other types of data designed to convey one or more types of information about the cardiac rhythms of patient 14 in an intuitive way.

For instance, in one example, the first data indicates whether the generalized CRC has identified an occurrence of a particular cardiac arrhythmia in a segment of the cardiac EGM strip. In this example, the dashboard interface may include output data in the form of a first bar in a bar graph having a size proportional to the number of occurrences of the particular cardiac arrhythmia that have been identified by the generalized CRC. Likewise, in some examples, the second data may indicate whether the specialized CRC has identified an occurrence of the particular cardiac arrhythmia in the segment of the cardiac EGM strip. In this example, the bar graph may include a second bar having a size proportional to the number of occurrences of the particular cardiac arrhythmia that have been identified by the specialized CRC. In this way, the bar graph may enable a comparison of the numbers of occurrences of the particular arrhythmia that have been identified by the first and second CRCs.

In one example, the aspect of the cardiac rhythm of the current patient is a morphological aspect of occurrences of a cardiac arrhythmia that occur in the cardiac rhythm of patient 14. In this example, the first data may comprise first data regarding the morphological aspect of an occurrence of the cardiac arrhythmia represented in the segment of the cardiac EGM strip. Additionally, in this example, the second data may comprise second data regarding the morphological aspect of the occurrence of the cardiac arrhythmia represented in the segment of the cardiac EGM strip. The output data may comprise data comparing the first data regarding the morphological aspect of the occurrence and the second data regarding the morphological aspect of the occurrence. For instance, the output data may include a chart that shows difference between the first data regarding the morphological aspect of the occurrence and the second data regarding the morphological aspect of the occurrence.

In another example where the first data and the second data indicate whether the generalized and specialized CRCs identified an occurrence of a cardiac arrhythmia in a segment of a cardiac EGM strip, the dashboard interface may include sparklines indicating the frequencies of occurrences of the cardiac arrhythmia over time. Many other examples of output data are possible, such as the types of data described in examples provided elsewhere in this disclosure.

In some examples, the AI system may generate second output data based on a comparison of the second data to historical data generated by the specialized CRC based on earlier cardiac EGM strips from the current patient. For instance, the AI system may generate data indicating trends in the aspect of the cardiac rhythm of patient 14. In one example, the AI system may count the number of occurrences of a cardiac arrhythmia, as identified by the second, specialized CRC, during each time period (e.g., each day), and show the counts in the form of a table or graph.

The AI system may present the output data to one or more types of users. For example, the AI system may present the output data to patient 14, a healthcare provider of patient 14, a user at a healthcare monitoring organization, or another type of person.

Figure 6:
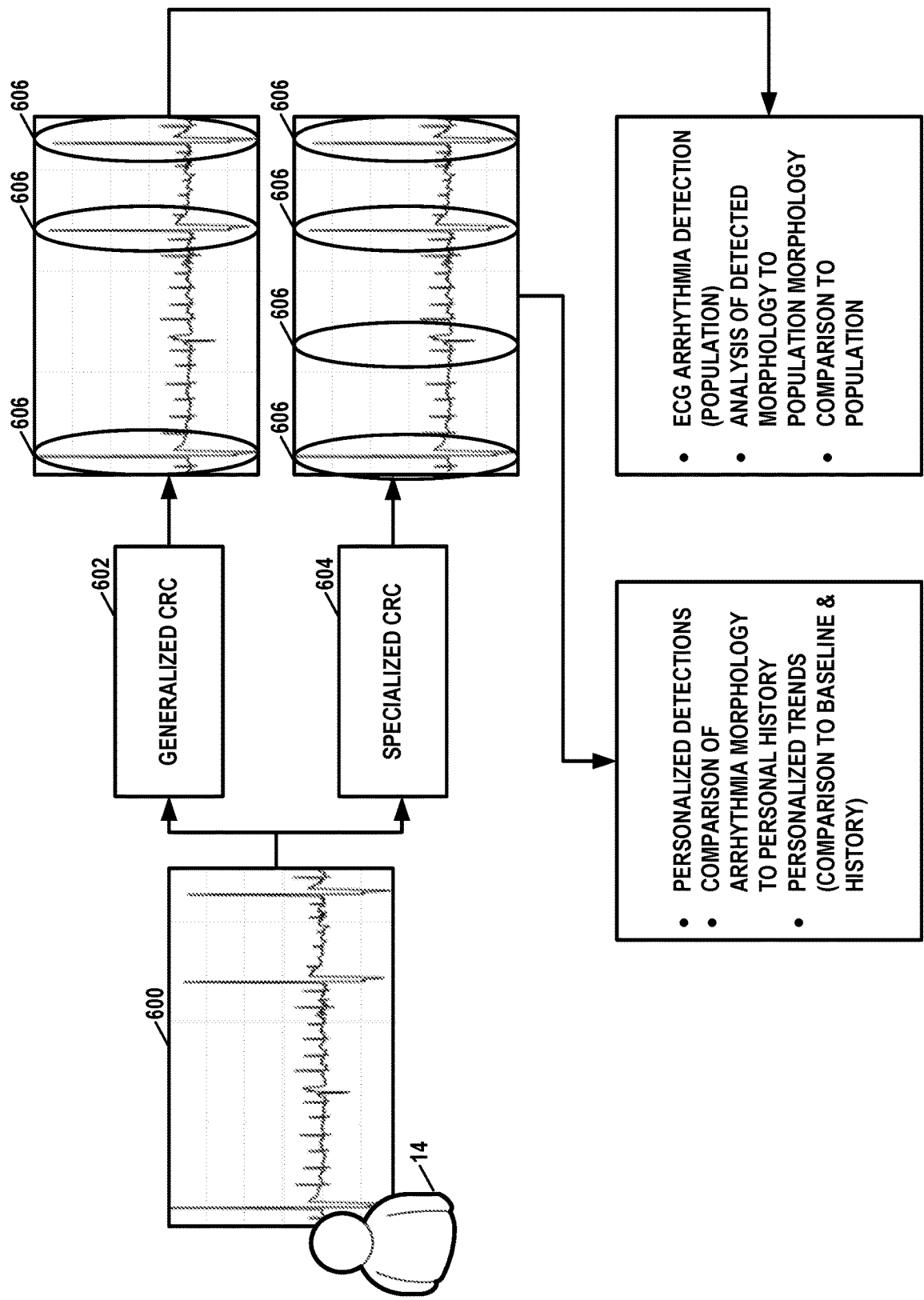
FIG. 6 is a conceptual diagram illustrating an example in which a generalized cardiac rhythm classifier (CRC) is updated based on cardiac electrograms (EGMs) of an individual patient in accordance with the techniques of this disclosure.
Figure 9:
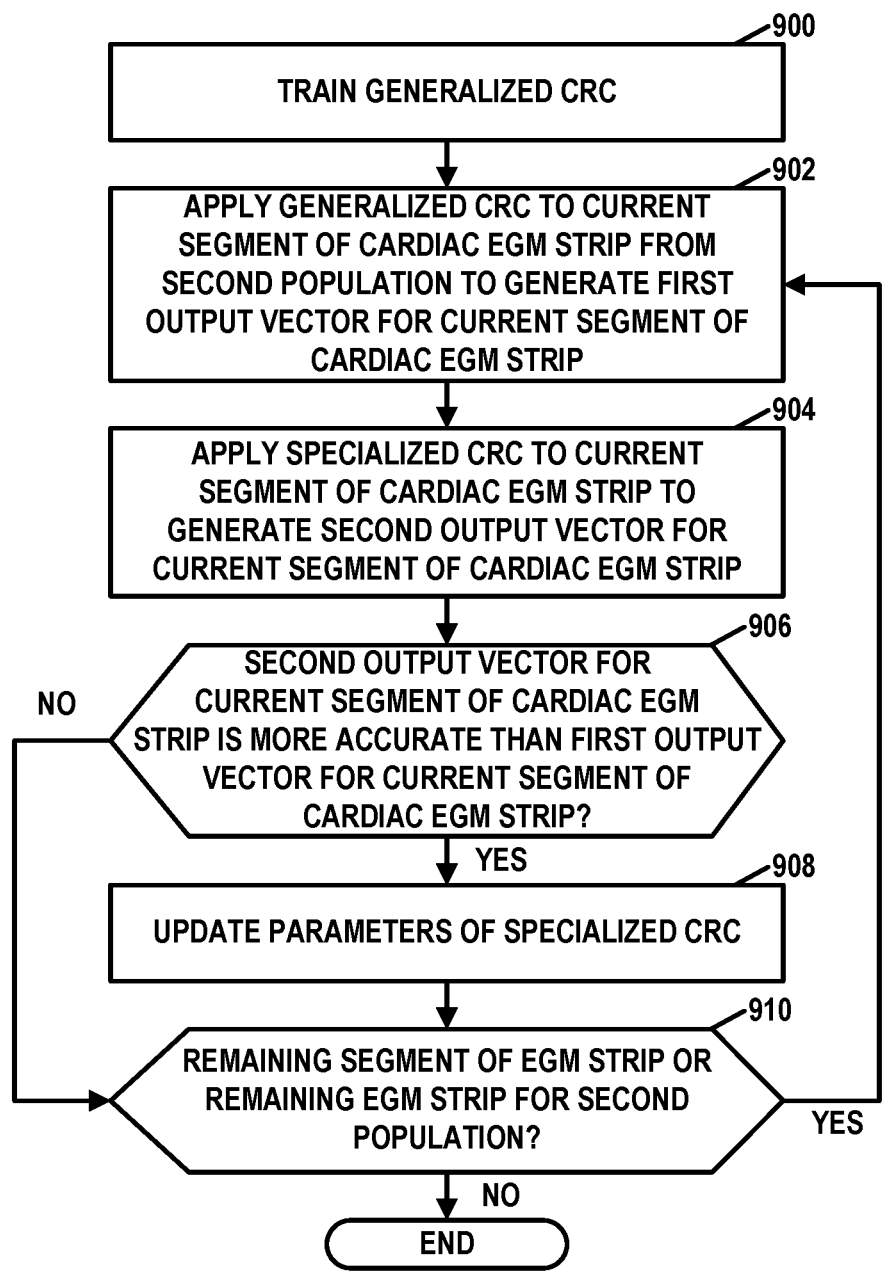
FIG. 9 is a flowchart illustrating an example operation for training a specialized CRC in accordance with the techniques of this disclosure.

FIG. 6 is a conceptual diagram illustrating an example in which a generalized CRC 602 is updated based on cardiac EGMs of an individual patient in accordance with the techniques of this disclosure. Generalized CRC 602 is trained based on cardiac EGM strips of a first population may be further trained based on cardiac EGM strips of a particular patient to generate a specialized CRC 604 for the particular patient. For instance, in an example where generalized CRC 602 is trained to generate data regarding one or more aspects of cardiac arrhythmias occurring in the cardiac rhythms of patients, the AI system may further train generalized CRC 602 based on cardiac EGM strips of patient 14 to generate data regarding the one or more aspects of cardiac arrhythmias occurring in the cardiac rhythm of patient 14. Thus, when the AI system starts monitoring of patient 14, specialized CRC 604 may be the same as generalized CRC 602. However, as time goes on, the AI system may selectively retrain specialized CRC 604 for patient 14 based on patient data (e.g., EGM strips) for patient 14. For instance, computing system 24 may apply a backpropagation algorithm to update parameters (e.g., weight values, bias values, etc.) associated with inputs to one or more layers of neurons in specialized CRC 604 for patient 14. FIG. 9, which is described in greater detail elsewhere in this disclosure, is a flowchart illustrating an example operation for training specialized CRCs.

As shown in the example of FIG. 6, the AI system may obtain a cardiac EGM strip 600 of patient 14. Furthermore, the AI system may apply generalized CRC 602 and specialized CRC 604 with a segment of the cardiac EGM strip 600 as input. In the example of FIG. 6, generalized CRC 602 and specialized CRC 604 identify occurrence of one or more cardiac arrhythmias in the cardiac rhythms represented by cardiac EGM strips. In the example of FIG. 6, identified occurrences of the cardiac arrhythmias are marked with ovals 606. Furthermore, as shown in the example of FIG. 6, generalized CRC 602 may identify three occurrences of the cardiac arrhythmias when segments of cardiac EGM strip 600 are provided as input to generalized CRC 602. However, as shown in the example of FIG. 6, specialized CRC 604 may identify four occurrences of the cardiac arrhythmia when the segments of cardiac EGM strip 600 are provided as input to specialized CRC 604. Specialized CRC 604 may be able to identify the additional occurrence because morphological aspects of occurrences of a particular cardiac arrhythmia occurring in patient 14 may differ in some way from the morphological aspects of occurrences of the particular cardiac arrhythmia occurring in the general population upon which generalized CRC 602 is trained.

Furthermore, as shown in the example of FIG. 6, the AI system may generate various types of output data based on data generated by generalized CRC 602 and specialized CRC 604. For example, the AI system may generate output data indicating personalized detections of occurrences of a cardiac arrhythmia.

In some examples, the AI system may generate output data indicating a comparison of a morphological attribute of an occurrence of a cardiac arrhythmia detected by specialized CRC 604 to a morphological attribute of occurrences of the cardiac arrhythmia previously detected by specialized CRC 604. For instance, in this example, the AI system may apply specialized CRC 604 to segments of cardiac EGM strips of patient 14 to identify occurrences of one or more cardiac arrhythmias. Example morphological attributes may include QRS width, number of unique premature ventricular contraction (PVC) morphologies, mean heart rate of the detected arrhythmia, P-R intervals, and so on. Furthermore, the AI system may generate values for a morphological attribute of the identified occurrences of the cardiac arrhythmias. The AI system may then use the values for the morphological attribute of the identified occurrences of the cardiac arrhythmias to generate comparison data that enables a user to compare the values for the morphological attribute of the identified occurrences of the cardiac arrhythmias.

For instance, in an example where the cardiac arrhythmia is atrial fibrillation, the morphological attribute may be the temporal duration or ventricular rate during atrial fibrillation of occurrences of atrial fibrillation. In this example, the AI system may apply specialized CRC 604 to segments of cardiac EGM strips of patient 14 to identify occurrences of atrial fibrillation. Furthermore, in this example, for each of the identified occurrences of atrial fibrillation, the AI system may determine a temporal duration value that indicates a temporal duration of the identified occurrence of atrial fibrillation. In this example, the AI system may then use the determined temporal duration values to generate comparison data. For instance, in this example, the comparison data may include a line chart showing a trend of the determined temporal duration values. In some examples, the comparison data may list the determined temporal duration values.

In some examples, the AI system may generate output data indicating personalized trends for patient 14. For instance, in one example, the AI system may generate output data showing changes over time to morphological attributes in occurrences of a cardiac arrhythmia identified by specialized CRC 604, changes over time to frequencies of occurrences of the cardiac arrhythmia identified by specialized CRC 604, and so on.

In some examples, the AI system may apply generalized CRC 602 and specialized CRC 604 to segments of the same set of cardiac EGM strips of patient 14 to identify occurrences of one or more cardiac arrhythmias. Thus, the AI system may identify a first set of occurrences by applying generalized CRC 602 and a second set of occurrences by applying specialized CRC 604. In this example, computing system 24 may generate comparison data based on the first set of occurrence and the second set of occurrences. In some examples, the comparison data may serve to emphasize the worth of the using specialized CRC 604 by providing a comparison of the number of occurrences in the first set of occurrences and the second set of occurrences.

In some examples, the AI system may perform an analysis of a morphological attribute of occurrences of a cardiac arrhythmia identified by specialized CRC 604 and the morphological attribute of occurrences of the cardiac arrhythmia identified by generalized CRC 602. For instance, in one example, the AI system may identify a first set of occurrences of the cardiac arrhythmia by applying generalized CRC 602 to segments of a set of cardiac EGM strips of patient 14. In this example, the AI system may identify a second set of occurrences of the cardiac arrhythmia by applying specialized CRC 604 to the segments of the same set of cardiac EGM strips of patient 14. Furthermore, in this example, the AI system may generate a first set of values for a morphological attribute of the occurrences of the cardiac arrhythmia identified by generalized CRC 602. Similarly, in this example, the AI system may generate a second set of values for the morphological attribute of the occurrences of the cardiac arrhythmia. The AI system may then generate comparison data that enables a user to compare the values for the morphological attribute in the occurrences of the cardiac arrhythmia identified by generalized CRC 602 and specialized CRC 604. Furthermore, the comparison data may include data indicating a value of the morphological attribute of the occurrences of the cardiac arrhythmia in members of the general population.

Figure 7:
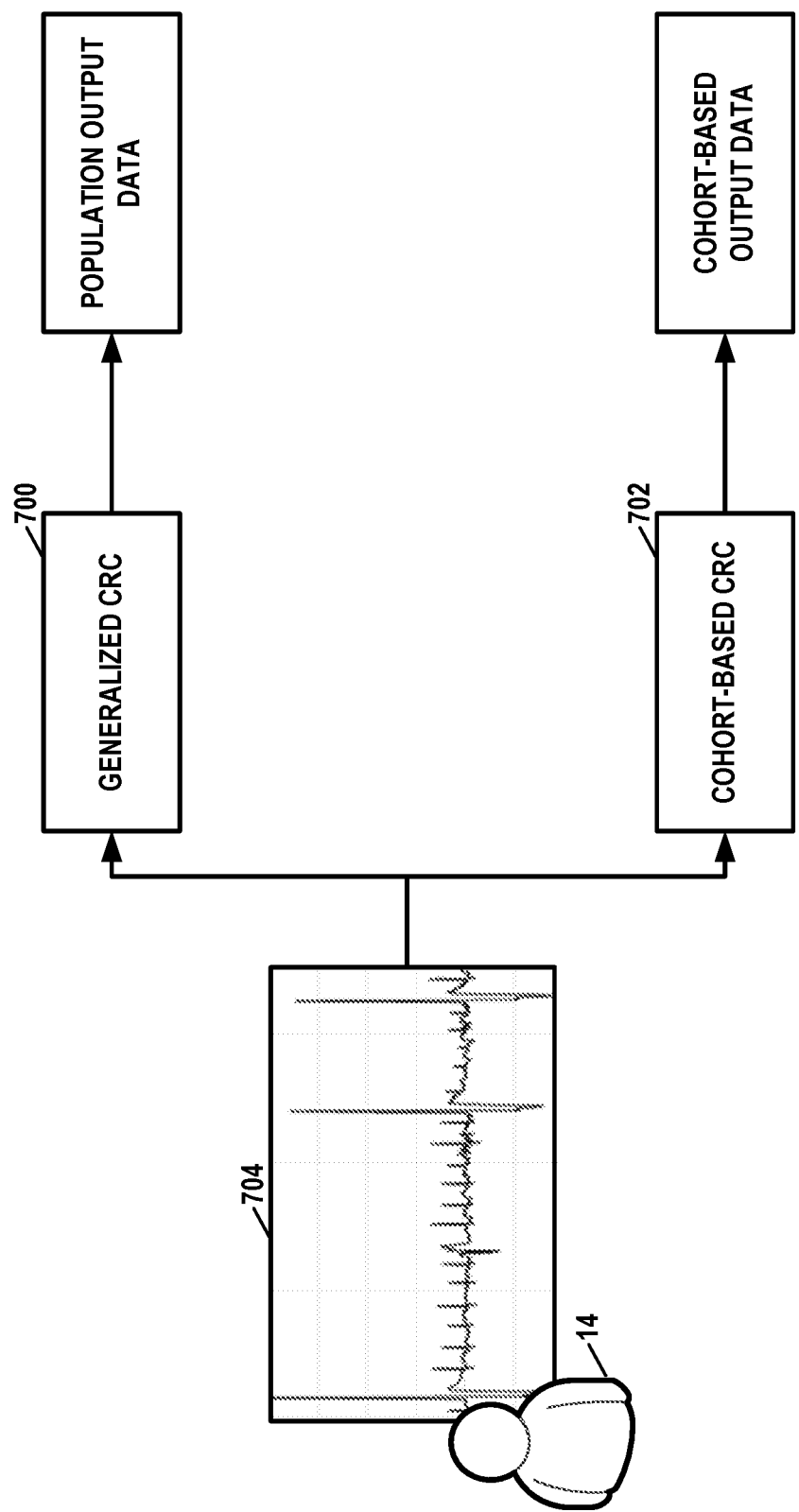
FIG. 7 is a conceptual diagram illustrating an example in which a computing system applies a generalized CRC and a cohort-based CRC in accordance with the techniques of this disclosure.

FIG. 7 is a conceptual diagram illustrating an example in which computing system 24 applies a generalized CRC 700 and a cohort-based specialized CRC 702 in accordance with the techniques of this disclosure. Similar to the example of FIG. 6, computing system 24 may obtain a cardiac EGM strip 704 of patient 14.

In the example of FIG. 7, instead of being trained on data from all patients in a population (e.g., a population of patients being monitored by monitoring system 450 (FIG. 4)), a set of one or more specialized CRCs, such as cohort-based CRC 702, are trained based on specific patient cohorts. The patient cohorts may be defined in any of various ways. For example, a patient cohort may be defined based on diagnosis and procedure codes, such as codes defined in the $10^{th}$ revision of the International Statistical Classification of Diseases and Related Health Problems (ICD-10) and Current Procedural Technology (CPT) codes. In this example, cohort-based CRC 702 may be trained based on segments of EGM strips and, in some examples, other patient data of a select group of patients, all of which have a shared ICD-10 and/or CPT code history in their medical records. Thus, data generated by cohort-based CRC 702 may reflect the physiology of the select group of patients.

The AI system may generate output data that enable a user to compare two or more of data regarding patient 14, data regarding a patient cohort, and/or data regarding the population on which generalized CRC 700 was trained. For example, the AI system may generate output data of any of the types described with respect an individual patient in FIG. 6 with a cohort instead of the individual patient.

In some examples, the AI system may also apply a specialized CRC for an individual patient (e.g., patient 14). Thus, the AI system may generate output data that may enable a user to compare the individual's data with data generated by generalized CRC 700 and cohort-based CRC 702, so that a user may see that individual's data compared to both the general population as well as others with similar diagnoses and procedural histories.

In some examples, the AI system may determine, based on the data generated by a plurality of cohort-based CRCs and data generated by a personalized CRC for an individual patient, which of the cohort-based CRCs generates data most like the data generated by the personalized CRC for the individual patient. For instance, the AI system may calculate a mean square error, sum of absolute differences, or other metrics of determining the similarity between data generated by a cohort-based CRC and data generated by the personalized CRC for the individual patient. In this way, the AI system may determine which of the cohort-based CRCs (and hence which one of the patient cohorts) is most like the individual patient. This may enable better association between the individual patient and a patient cohort than general demographic information. For instance, the AI system may determine that the individual patient is in their mid-50s but has a cardiac rhythm profile of someone in their mid-40s. In some examples, the AI system may generate a notification in response to determining that the individual patient is better associated with a particular patient cohort than a patient cohort currently associated with the individual patient.

Figure 8:
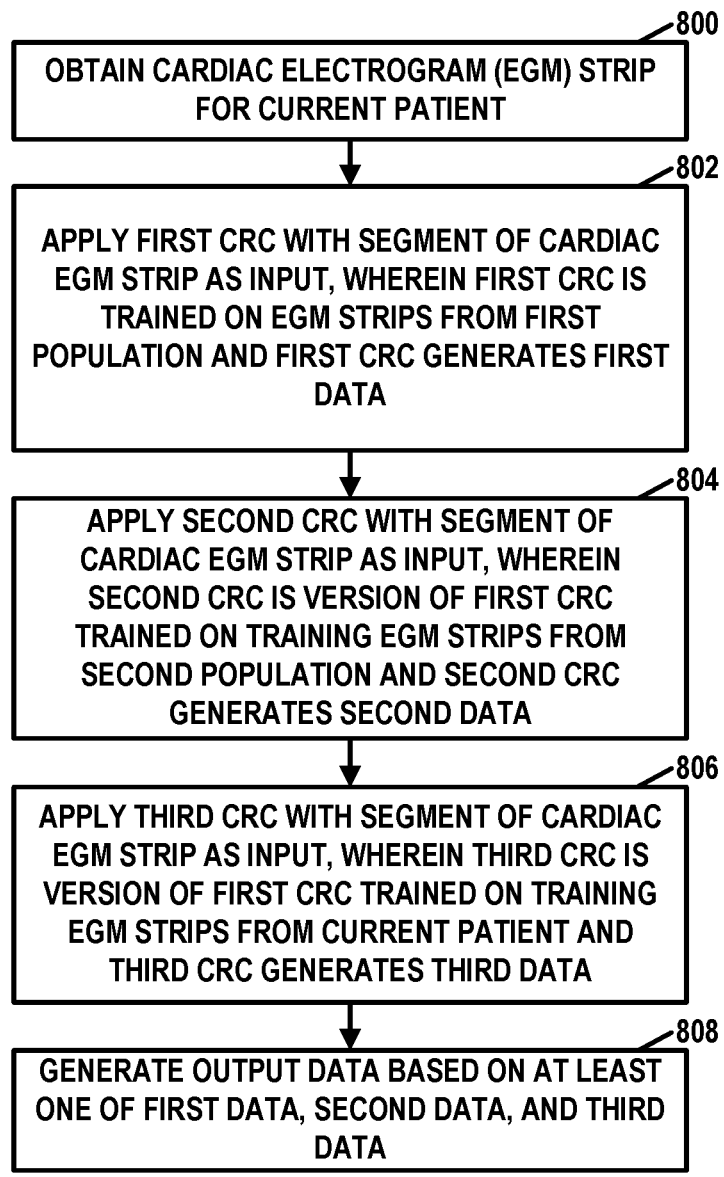
FIG. 8 is a flowchart illustrating an example operation in which a computing system applies a generalized CRC, a cohort-based CRC, and a specialized CRC in accordance with the techniques of this disclosure.

FIG. 8 is a flowchart illustrating an example operation in which a computing system applies a generalized CRC, a cohort-based CRC, and a specialized CRC in accordance with the techniques of this disclosure. In the example of FIG. 8, the AI system may obtain a cardiac EGM strip for patient 14 (i.e., a current patient) (800). Additionally, the AI system may apply a first CRC (e.g., a generalized CRC) with a segment of the cardiac EGM strip as input (802). The first CRC is trained on EGM strips from a first population. The first CRC generates first data. The AI system may apply the first CRC in the same manner as described with respect to action (502) of FIG. 5.

Furthermore, in the example of FIG. 8, the AI system may apply a second CRC (e.g., a cohort-based CRC) with the segment of the cardiac EGM strip as input (804). The second CRC is trained on EGM strips from a second population, such as a patient cohort. The second CRC generates second data. Additionally, in the example of FIG. 8, the AI system may apply a third CRC (e.g., a specialized CRC for patient 14) with the segment of the cardiac EGM strip as input (806). The third CRC is trained on EGM strips from patient 14. The third CRC generates third data. In some examples, the third CRC is a version of the first CRC that is trained based on the training cardiac EGM strips from the first population and further trained based only on training cardiac EGM strips from patient 14.

The AI system may generate output data based on at least one of the first data, second data, and third data (808). For instance, the AI system may generate output data that includes charts, graphs, and other types of data that enable any of the various types of comparisons described elsewhere in this disclosure and others.

FIG. 9 is a flowchart illustrating an example operation for training a specialized CRC in accordance with the techniques of this disclosure. In the example of FIG. 9, the AI system may train a generalized CRC based on segments of EGM strips for patients in a first population (900). The AI system may train the generalized CRC in accordance with any of the examples provided elsewhere in this disclosure. Furthermore, the AI system may generate a specialized CRC. For instance, the AI system may generate the specialized CRC by training an instance of the first CRC based on (e.g., only on) cardiac EGM strips from the second population. The AI system may perform actions (902)-(910) to generate the specialized CRC.

Furthermore, in the example of FIG. 9, the AI system may apply the generalized CRC to a current segment of a cardiac EGM strip from a second population to generate a first output vector for the current segment of the cardiac EGM strip (902). The second population may be smaller than the first population. For instance, the second population may be limited to a single patient or a cohort of patients. An output vector is a vector of elements, such as numerical or Boolean values, generated by a CRC. Additionally, in the example of FIG. 9, the AI system may apply a specialized CRC to the current segment of the cardiac EGM strip to generate a second output vector for the current segment of the cardiac EGM strip (904).

Next, the AI system may determine whether the second output vector for the current segment of the cardiac EGM strip is more accurate than the first output vector for the current segment of the cardiac EGM strip (906). The AI system may make this determination in any of one or more ways. For instance, in one example, the first output vector and the second output vectors include likelihood values that indicate likelihoods of the current segment of the cardiac EGM strip include occurrences of cardiac arrhythmias. In this example, the AI system may compare the likelihood values generated by the generalized CRC and the specialized CRC. In this example, it is preferable to have a higher likelihood corresponding to the presence of a cardiac arrhythmia per human review and a lower likelihood value corresponding to the absence of a cardiac arrhythmia per human review. The AI system may also compare the output vectors on an annotated dataset for overall accuracy (e.g., based on sensitivity and specificity).

In response to determining that the second output vector is more accurate than the first output vector ("YES" branch of 906), the AI system may update the parameters of the specialized CRC (908). For example, the AI system may apply an error function that calculates an error between an expected output vector of the specialized CRC and an actual output vector of the specialized CRC. In this example, the AI system may use this error function in a backpropagation algorithm to update the parameters of the specialized CRC.

After updating the parameters of the specialized CRC or in response to determining that the second output vector is not more accurate than the first output vector ("NO" branch of 906), the AI system may determine whether there are any remaining segments of the cardiac EGM strip or any remaining EGM strips for the second population (910). If there are one or more remaining segments of the cardiac EGM strip or remaining EGM strips for the second population ("YES" branch of 910), the AI system may repeat actions 902-910 with another segment or EGM strip for the second population as the current segment and/or cardiac EGM strip. Otherwise ("NO" branch of 910), the training operation of FIG. 9 may end.

Training the specialized CRC in this way may help to guarantee that the accuracy of output vectors generated by the specialized CRC is not worse than the accuracy of the output vectors generated by the generalized CRC. Furthermore, training the specialized CRC in this way may be more efficient and consume less computational resource than training the specialized CRC on all segments of the EGM strips.

In some examples, the AI system is configured to perform a process to train the specialized CRC in response to receiving an indication of user input to do so. For instance, the AI system may receive an indication of user input indicating that the AI system is to train the specialized CRC based on a specific cardiac EGM strip.

Figure 10:
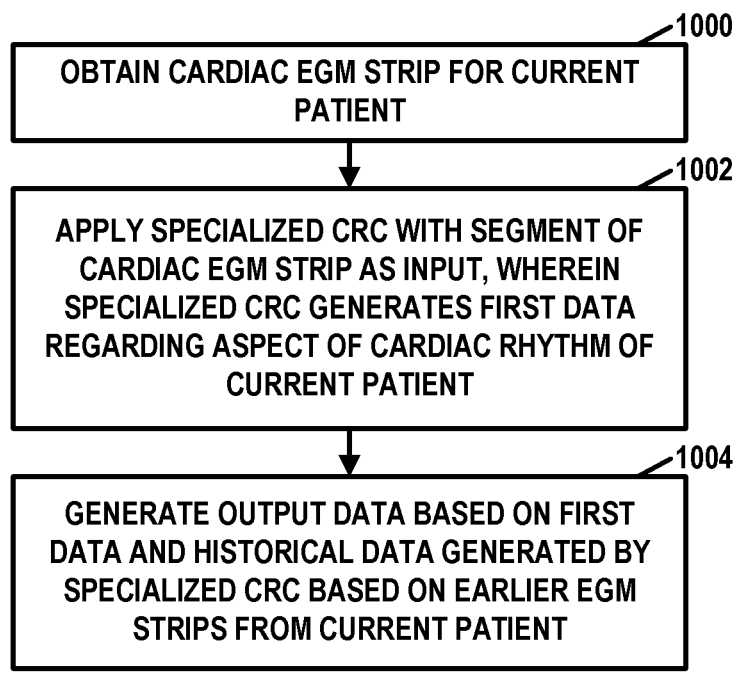
FIG. 10 is a flowchart illustrating an example operation for generation of personalized output data in accordance with the techniques of this disclosure.

FIG. 10 is a flowchart illustrating an example operation for generation of personalized output data in accordance with the techniques of this disclosure. In the example of FIG. 10, the AI system may obtain a cardiac EGM strip for a current patient (1000). Additionally, the AI system may apply a personalized CRC with a segment of the cardiac EGM strip as input (1002). In the example of FIG. 10, the specialized CRC is trained on training cardiac EGM strips from the current patient. The specialized CRC generates, based on the segment of the cardiac EGM strip, first data regarding an aspect of a cardiac rhythm of the current patient. The aspect of the cardiac rhythm may be a cardiac arrhythmia, a morphological aspect of a cardiac rhythm, an R-R interval of the current patient, or another aspect of the cardiac rhythm of the current patient.

Furthermore, in the example of FIG. 10, the AI system generates output data based on the first data and historical data generated by the specialized CRC based on earlier cardiac EGM strips from the current patient (1004). Thus, in the example of FIG. 10, the specialized CRC is not necessarily trained or otherwise based on training data from a larger population. Rather, the specialized CRC may be trained only based on training data for the current patient. In some examples, the output data indicates a trend of the aspect of the cardiac rhythm of the current patient. In some examples, the cardiac EGM strip is from after an event and each of the earlier cardiac EGM strips are from before the event. In this example, the output data comprises a comparison of the aspect of the cardiac rhythm of the current patient before and after the event. Example events may include implantation of a medical device, a surgical procedure, a change in medicine taken by the current patient, development of a new cardiac arrhythmia, and so on.

Figure 11:
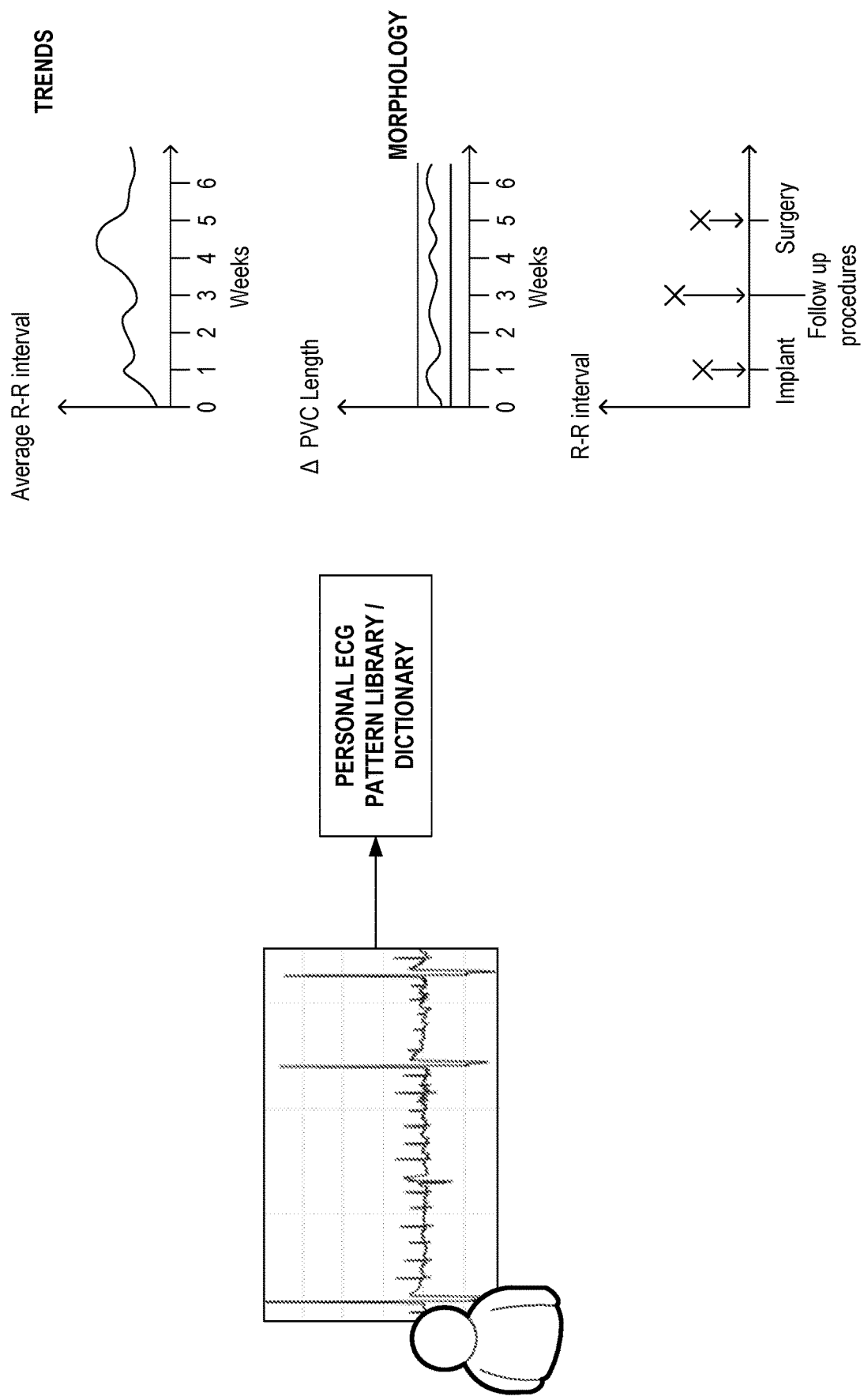
FIG. 11 is a conceptual diagram illustrating an example in which a computing system generates personalized output data in accordance with the techniques of this disclosure.

FIG. 11 is a conceptual diagram illustrating an example in which a computing system generates personalized output data in accordance with the techniques of this disclosure. FIG. 11 is consistent with the example operation of FIG. 10. In the example of FIG. 11, an arrhythmia pattern dictionary is constructed for every patient, based purely on data from the individual patient. All data from a single patient is used to train a neural network to score the cardiac arrhythmias and normal rhythms that occur in that patient's history. Unlike a standard classifier, this type of personalized CRC may not be the best to flag adverse conditions. Adverse conditions may be better identified by a more generalized CRC. However, the personalized CRC may be valuable in trending long-term data for a single patient.

The outputs of the personalized CRC may be used for one or more of various purposes. For example, the outputs of the personalized CRC may be used to score and trend changes from the patient's own baseline. For instance, in this example, the AI system may generate output data indicating trends regarding one or more aspects of a cardiac rhythm of patient 14 from a time following implantation of a monitoring device in patient 14 (e.g., medical device 16). In this example, the one or more aspects of the cardiac rhythm may include R-R intervals over a time period (e.g., 1 week), frequency of occurrence of a particular cardiac arrhythmia, and so on.

In another example, the outputs of the personalized CRC may be used to detect and score changes in one or more morphological aspects of detected occurrences of a cardiac arrhythmia compared to the morphological aspects of previously-detected occurrences of the cardiac arrhythmia. For instance, the outputs of the personalized CRC may be used to detect and track changes in the average line-length of premature ventricular contractions (PVCs). In another example, the output of the personalized CRC may illustrate changes in the patient's data as a function of changes in medication or new procedures performed.

A personalized CRC trained on a single subject's data could also be designed to have a smaller computational footprint (hardware and software), as compared to larger population models, and hence could run on smaller hardware platforms like mobile devices and implanted hardware. For example, if the underlying model architecture for both the generalized and personalized CRCs is same (e.g., a 50-layer residual neural network), the model weights for the initial layers can be similar for both models. However, the model weights of the last few layers alone may be trained for the personalized CRC for that patient cohort. In terms of implementation, if both the generalized CRC and the personalized CRC have common computations corresponding to the initial layers of the neural network, these values from the generalized CRC can be used over in the personalized CRC (instead of repeating their computation) and the personalized CRC can have a smaller set of computation corresponding to only the last few neural network layers.

In some examples, the techniques of the disclosure include a system that comprises means to perform any method described herein. In some examples, the techniques of the disclosure include a computer-readable medium comprising instructions that cause processing circuitry to perform any method described herein.

The following is a non-limiting list of examples that are in accordance with one or more techniques of this disclosure.

Example 1A

A method comprising: obtaining, by a computing system, a cardiac electrogram (EGM) strip for a current patient; applying, by the computing system, a first cardiac rhythm classifier neural network (CRC) with a segment of the cardiac EGM strip as input, wherein: the first CRC is trained on training cardiac EGM strips from a first population that includes a plurality of patients, the first CRC generates, based on the segment of the cardiac EGM strip, first data regarding an aspect of a cardiac rhythm of the current patient; applying, by the computing system, a second CRC with the segment of the cardiac EGM strip as input, wherein: the second CRC is a version of the first CRC that is trained on training cardiac EGM strips from a second population that is smaller than the first population, the second CRC generates, based on the segment of the cardiac EGM strip, second data regarding the aspect of the cardiac rhythm of the current patient; and generating, by the computing system, output data based on the first data and the second data.

Example 2A

The method of claim 1A, wherein the second population consists of the current patient.

Example 3A

The method of claim 1A, wherein the second population is a cohort of patients sharing one or more characteristics with the current patient.

Example 4A

The method of claim 3A, wherein the one or more characteristics include a diagnosis of the cohort of patients and the current patient.

Example 5A

The method of claim 3A, wherein: the method further comprises applying, by the computing system, a third CRC with the cardiac EGM strip as input, wherein: the third CRC is a version of the first CRC that is trained based on the training cardiac EGM strips from the first population and further trained based only on training cardiac EGM strips from the current patient, and the third CRC generates, based on the segment of cardiac EGM strip, third data regarding the aspect of the cardiac rhythm of the current patient, and generating the output data comprises generating the output data based on the first data, the second data, and the third data.

Example 6A

The method of claim 1A, wherein: the aspect of the cardiac rhythm of the current patient is an occurrence of an occurrence of a cardiac arrhythmia in the cardiac rhythm of the current patient, the first data is based on a first probability that the segment of the cardiac EGM strip represents at least one occurrence of the cardiac arrhythmia, and the second data is based on a second probability that the segment of the cardiac EGM strip represents at least one occurrence of the cardiac arrhythmia.

Example 7A

The method of claim 1A, wherein: the aspect of the cardiac rhythm of the current patient is a morphological aspect of occurrences of a cardiac arrhythmia that occur in the cardiac rhythm of the current patient, the first data comprises first data regarding the morphological aspect of an occurrence of the cardiac arrhythmia represented in the segment of the cardiac EGM strip, the second data comprises second data regarding the morphological aspect of the occurrence of the cardiac arrhythmia represented in the segment of the cardiac EGM strip, and the output data comprises data comparing the first data regarding the morphological aspect of the occurrence and the second data regarding the morphological aspect of the occurrence.

Example 8A

The method of any of claims 1A-7A, further comprising: generating second output data based on a comparison of the second data to historical data generated by the second CRC based on earlier cardiac EGM strips from the current patient.

Example 9A

The method of any of claims 1A-8A, wherein: the first CRC generates an output vector, and the method further comprises generating, by the computing system, the second CRC by training an instance of the first CRC based only on cardiac EGM strips from the second population, wherein generating the second CRC comprises, for each respective segment of each respective cardiac EGM strip from the second population: applying, by the computing system, the first CRC to the respective segment of the respective cardiac EGM strip to generate a first output vector for the respective cardiac EGM strip; applying, by the computing system, the second CRC to the respective segment of the respective cardiac EGM strip to generate a second output vector for the respective cardiac EGM strip; determining, by the computing system, whether the second output vector for the respective segment of the respective cardiac EGM strip is more accurate than the first output vector for the respective cardiac EGM strip; updating, by the computing system, parameters of the second CRC based on whether the second output vector for the cardiac EGM strip is more accurate than the first output vector for the respective cardiac EGM strip, wherein: the computing system is configured to update the parameters of the second CRC when the second output vector for the cardiac EGM strip is more accurate than the first output vector for the respective cardiac EGM strip, and the computing system is configured to not update the parameters of the second CRC when the second output vector for the cardiac EGM strip is not more accurate than the first output vector for the respective cardiac EGM strip.

Example 1B

A method comprising: obtaining, by a computing system, a cardiac EGM strip for a current patient; applying, by the computing system, a specialized cardiac rhythm classifier (CRC) with a segment of the cardiac EGM strip as input, wherein: the specialized CRC is trained on training cardiac EGM strips from the current patient, and the specialized CRC generates, based on the segment of the cardiac EGM strip, first data regarding an aspect of a cardiac rhythm of the current patient; generating, by the computing system, output data based on the first data and historical data generated by the specialized CRC based on earlier cardiac EGM strips from the current patient.

Example 2B

The method of claim 1B, wherein the output data indicates a trend of the aspect of the cardiac rhythm of the current patient.

Example 3B

The method of claim 2B, wherein the aspect of the cardiac rhythm is an R-R interval of the current patient.

Example 4B

The method of claim 2B, wherein the aspect of the cardiac rhythm is a cardiac arrhythmia.

Example 5B

The method of claim 4B, wherein the aspect of the cardiac rhythm is a morphological aspect of the cardiac arrhythmia of the current patient.

Example 6B

The method of claim 2B, wherein: the cardiac EGM strip is from after an event and each of the earlier cardiac EGM strips are from before the event, and the output data comprises a comparison of the aspect of the cardiac rhythm of the current patient before and after the event.

Example 7B

The method of claim 6B, wherein the event is one of: implantation of a medical device, a surgical procedure, a change in medicine taken by the current patient, or development of a new cardiac arrhythmia.

Example 1C

A computing system comprising processing circuitry and a storage medium, the computing device configured to perform the methods of any of claims 1A-7B.

Example 2C

A computer-readable data storage medium having instructions stored thereon that, when executed, cause a computing system to perform the methods of any of claims 1A-7B.

Example 3C

A method as described in the specification.

It should be understood that various aspects and examples disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method for operating processing circuitry of a computing system, the method comprising:
   obtaining, by the processing circuitry of the computing system, a cardiac electrogram (EGM) strip for a current patient;
   applying, by the processing circuitry of the computing system, a first cardiac rhythm classifier neural network (CRC) with a segment of the cardiac EGM strip as input to generate, based on the segment of the cardiac EGM strip, first data indicating an aspect of a cardiac rhythm of the current patient, wherein, the aspect of the cardiac rhythm of the current patient comprises a morphological aspect of occurrences of a cardiac arrhythmia that occur in the cardiac rhythm of the current patient, the first CRC is trained on training cardiac EGM strips from a first population that includes a plurality of patients, and the first data, generated by the first CRC, comprises first data indicating the morphological aspect of an occurrence of the cardiac arrhythmia represented in the segment of the cardiac EGM strip;
   applying, by the processing circuitry of the computing system, a second CRC with the segment of the cardiac EGM strip as input to generate, based on the segment of the cardiac EGM strip, second data indicating the aspect of the cardiac rhythm of the current patient, wherein the second CRC is a version of the first CRC that is trained on training cardiac EGM strips from a second population that is smaller than the first population and the second data, generated by the second CRC, comprises second data indicating the morphological aspect of the occurrence of the cardiac arrhythmia represented in the segment of the cardiac EGM strip; and
   generating, by the processing circuitry of the computing system, output data including comparison data based on a comparison of the first data indicating the morphological aspect of the occurrence of the cardiac arrhythmia represented in the segment of the cardiac EGM strip and the second data indicating the morphological aspect of the occurrence of the cardiac arrhythmia represented in the segment of the cardiac EGM strip.

2. The method of claim 1, wherein the second population consists of the current patient.

3. The method of claim 1, wherein the second population is a cohort of patients sharing one or more characteristics with the current patient.

4. The method of claim 3, wherein the one or more characteristics include a diagnosis of the cohort of patients and the current patient.

5. The method of claim 3, wherein:
   the method further comprises applying, by the computing system, a third CRC with the cardiac EGM strip as input to generate based on the segment of cardiac EGM strip, third data indicating the aspect of the cardiac rhythm of the current patient, wherein, the third CRC is a version of the first CRC that is trained based on the training cardiac EGM strips from the first population and further trained based only on training cardiac EGM strips from the current patient, and the third data, generated by the third CRC, comprises third data indicating the morphological aspect of an occurrence of the cardiac arrhythmia represented in the segment of the cardiac EGM strip; and
   generating the output data comprises generating the output data including second comparison data based on a comparison of the first data indicating the morphological aspect of the occurrence of the cardiac arrhythmia represented in the segment of the cardiac EGM strip, the second data indicating the morphological aspect of the occurrence of the cardiac arrhythmia represented in the segment of the cardiac EGM strip, and the third data indicating the morphological aspect of the occurrence of the cardiac arrhythmia represented in the segment of the cardiac EGM strip.

6. The method of claim 1, further comprising:
   generating second output data based on a comparison of the second data to historical data generated by the second CRC based on earlier cardiac EGM strips from the current patient.

7. The method of claim 1, wherein:
   the first CRC generates an output vector, and
   the method further comprises generating, by the processing circuitry of the computing system, the second CRC by training an instance of the first CRC based only on cardiac EGM strips from the second population, wherein generating the second CRC comprises, for each respective segment of each respective cardiac EGM strip from the second population:
   applying, by the processing circuitry of the computing system, the first CRC to the respective segment of the respective cardiac EGM strip to generate a first output vector for the respective cardiac EGM strip;
   applying, by the processing circuitry of the computing system, the second CRC to the respective segment of the respective cardiac EGM strip to generate a second output vector for the respective cardiac EGM strip;
   determining, by the processing circuitry of the computing system, whether the second output vector for the respective segment of the respective cardiac EGM strip is more accurate than the first output vector for the respective cardiac EGM strip;
   updating, by the processing circuitry of the computing system, parameters of the second CRC based on whether the second output vector for the cardiac EGM strip is more accurate than the first output vector for the respective cardiac EGM strip, wherein:
   the processing circuitry of the computing system is configured to update the parameters of the second CRC when the second output vector for the cardiac EGM strip is more accurate than the first output vector for the respective cardiac EGM strip, and the processing circuitry of the computing system is configured to not update the parameters of the second CRC when the second output vector for the cardiac EGM strip is not more accurate than the first output vector for the respective cardiac EGM strip.

8. A method for operating processing circuitry of a computing system, the method comprising:

obtaining, by the processing circuitry of the computing system, a cardiac electrogram (EGM) strip for a current patient;

applying, by the processing circuitry of the computing system, a first cardiac rhythm classifier neural network (CRC) with a segment of the cardiac EGM strip as input to generate, based on the segment of the cardiac EGM strip, first data indicating an aspect of a cardiac rhythm of the current patient, wherein the aspect of the cardiac rhythm of the current patient is an occurrence of a cardiac arrhythmia in the cardiac rhythm of the current patient, the first CRC is trained on training cardiac EGM strips from a first population that includes a plurality of patients, and the first data is based on a first probability that the segment of the cardiac EGM strip represents at least one occurrence of the cardiac arrhythmia;

applying, by the processing circuitry of the computing system, a second CRC with the segment of the cardiac EGM strip as input to generate, based on the segment of the cardiac EGM strip, second data indicating the aspect of the cardiac rhythm of the current patient, wherein the second CRC is a version of the first CRC that is trained on training cardiac EGM strips from a second population that is smaller than the first population and the second data is based on a second probability that the segment of the cardiac EGM strip represents at least one occurrence of the cardiac arrhythmia; and generating, by the processing circuitry of the computing system, output data indicating a cardiac arrhythmia occurred in the cardiac rhythm of the current patient based on the second data.

9. A computing system comprising:

a storage medium configured to store a cardiac electrogram (EGM) strip for a current patient; and processing circuitry configured to:

apply a first cardiac rhythm classifier neural network (CRC) with a segment of the cardiac EGM strip as input to generate, based on the segment of the cardiac EGM strip, first data indicating an aspect of a cardiac rhythm of the current patient, wherein, the aspect of the cardiac rhythm of the current patient comprises a morphological aspect of occurrences of a cardiac arrhythmia that occur in the cardiac rhythm of the current patient, the first CRC is trained on training cardiac EGM strips from a first population that includes a plurality of patients, and the first data, generated by the first CRC, comprises first data indicating the morphological aspect of an occurrence of the cardiac arrhythmia represented in the segment of the cardiac EGM strip;

apply a second CRC with the segment of the cardiac EGM strip as input to generate, based on the segment of the cardiac EGM strip, second data indicating the aspect of the cardiac rhythm of the current patient, wherein the second CRC is a version of the first CRC that is trained on training cardiac EGM strips from a second population that is smaller than the first population and the second data, generated by the second CRC, comprises second data indicating the morphological aspect of the occurrence of the cardiac arrhythmia represented in the segment of the cardiac EGM strip; and generate output data including comparison data based on a comparison of the first data indicating the morphological aspect of the occurrence of the cardiac arrhythmia represented in the segment of the cardiac EGM strip and the second data indicating the morphological aspect of the occurrence of the cardiac arrhythmia represented in the segment of the cardiac EGM strip.

10. The computing system of claim 9, wherein the second population consists of the current patient.

11. The computing system of claim 9, wherein the second population is a cohort of patients sharing one or more characteristics with the current patient.

12. The computing system of claim 11, wherein the one or more characteristics include a diagnosis of the cohort of patients and the current patient.

13. The computing system of claim 11, wherein:

the processing circuitry is further configured to apply a third CRC with the cardiac EGM strip as input to generate based on the segment of cardiac EGM strip, third data indicating the aspect of the cardiac rhythm of the current patient, wherein, the third CRC is a version of the first CRC that is trained based on the training cardiac EGM strips from the first population and further trained based only on training cardiac EGM strips from the current patient, and the third data, generated by the third CRC, comprises third data indicating the morphological aspect of an occurrence of the cardiac arrhythmia represented in the segment of the cardiac EGM strip, and the processing circuitry is configured such that, as part of generating the output data, the processing circuitry generates the output data including second comparison data based on a comparison of the first data indicating the morphological aspect of the occurrence of the cardiac arrhythmia represented in the segment of the cardiac EGM strip, the second data indicating the morphological aspect of the occurrence of the cardiac arrhythmia represented in the segment of the cardiac EGM strip, and the third data indicating the morphological aspect of the occurrence of the cardiac arrhythmia represented in the segment of the cardiac EGM strip.

14. The computing system of claim 9, wherein the processing circuitry is further configured to:

generate second output data based on a comparison of the second data to historical data generated by the second CRC based on earlier cardiac EGM strips from the current patient.

15. The computing system of claim 9, wherein:

the first CRC generates an output vector, and the computing system is further configured to generate the second CRC by training an instance of the first CRC based only on cardiac EGM strips from the second population, wherein the processing circuitry is configured such that, as part of generating the second CRC, the processing circuitry, for each respective segment of each respective cardiac EGM strip from the second population:

applies the first CRC to the respective segment of the respective cardiac EGM strip to generate a first output vector for the respective cardiac EGM strip;

applies the second CRC to the respective segment of the respective cardiac EGM strip to generate a second output vector for the respective cardiac EGM strip;

determines whether the second output vector for the respective segment of the respective cardiac EGM strip is more accurate than the first output vector for the respective cardiac EGM strip;

updates parameters of the second CRC based on whether the second output vector for the cardiac EGM strip is more accurate than the first output vector for the respective cardiac EGM strip, wherein:
the processing circuitry is configured to update the parameters of the second CRC when the second output vector for the cardiac EGM strip is more accurate than the first output vector for the respective cardiac EGM strip, and
the processing circuitry is configured to not update the parameters of the second CRC when the second output vector for the cardiac EGM strip is not more accurate than the first output vector for the respective cardiac EGM strip.

16. A computing system comprising:
a storage medium configured to store a cardiac electrogram (EGM) strip for a current patient; and
processing circuitry configured to:
apply a first cardiac rhythm classifier neural network (CRC) with a segment of the cardiac EGM strip as input to generate, based on the segment of the cardiac EGM strip, first data indicating an aspect of a cardiac rhythm of the current patient, wherein the aspect of the cardiac rhythm of the current patient is an occurrence of a cardiac arrhythmia in the cardiac rhythm of the current patient, the first CRC is trained on training cardiac EGM strips from a first population that includes a plurality of patients, and the first data is based on a first probability that the segment of the cardiac EGM strip represents at least one occurrence of the cardiac arrhythmia;
apply a second CRC with the segment of the cardiac EGM strip as input to generate, based on the segment of the cardiac EGM strip, second data indicating the aspect of the cardiac rhythm of the current patient, wherein the second CRC is a version of the first CRC that is trained on training cardiac EGM strips from a second population that is smaller than the first population and the second data is based on a second probability that the segment of the cardiac EGM strip represents at least one occurrence of the cardiac arrhythmia; and
generate output data indicating a cardiac arrhythmia occurred in the cardiac rhythm of the current patient based on the second data.

17. A non-transitory computer-readable data storage medium having instructions stored thereon that, when executed, cause a computing system to:
obtain a cardiac electrogram (EGM) strip for a current patient;
apply a first cardiac rhythm classifier neural network (CRC) with a segment of the cardiac EGM strip as input to generate, based on the segment of the cardiac EGM strip, first data indicating an aspect of a cardiac rhythm of the current patient, wherein, the aspect of the cardiac rhythm of the current patient comprises a morphological aspect of occurrences of a cardiac arrhythmia that occur in the cardiac rhythm of the current patient, the first CRC is trained on training cardiac EGM strips from a first population that includes a plurality of patients, and the first data, generated by the first CRC, comprises first data indicating the morphological aspect of an occurrence of the cardiac arrhythmia represented in the segment of the cardiac EGM strip;
apply a second CRC with the segment of the cardiac EGM strip as input to generate, based on the segment of the cardiac EGM strip, second data indicating the aspect of the cardiac rhythm of the current patient, wherein the second CRC is a version of the first CRC that is trained on training cardiac EGM strips from a second population that is smaller than the first population and the second data, generated by the second CRC, comprises second data indicating the morphological aspect of the occurrence of the cardiac arrhythmia represented in the segment of the cardiac EGM strip; and
generate output data including data based on a comparison of the first data indicating the morphological aspect of the occurrence of the cardiac arrhythmia represented in the segment of the cardiac EGM strip and the second data indicating the morphological aspect of the occurrence of the cardiac arrhythmia represented in the segment of the cardiac EGM strip.

* * * * *